United States Patent [19]

Shimanuki et al.

[11] Patent Number: 5,307,385

[45] Date of Patent: Apr. 26, 1994

[54] METHOD OF AND APPARATUS FOR ESTIMATING REMAINING SERVICE LIFE OF MATERIAL BEING EXPOSED TO RADIANT RAY IRRADIATION

[75] Inventors: Shizuka Shimanuki, Hitachi; Kiyotomo Nakata, Katsuta; Shizuo Matushita, Hitachi; Shigeki Kasahara, Hitachi; Michiyoshi Yamamoto, Hitachi; Hideya Anzai, Hitachi, all of Japan

[73] Assignee: Hitachi, Ltd., Tokyo, Japan

[21] Appl. No.: 895,049

[22] Filed: Jun. 8, 1992

[30] Foreign Application Priority Data

Jun. 6, 1991 [JP] Japan ................... 3-135188

[51] Int. Cl.$^5$ ............................................. G21C 17/00
[52] U.S. Cl. ........................... 376/249; 376/245; 376/305
[58] Field of Search ............... 376/159, 245, 153, 154, 376/249, 305; 250/390.01; 976/DIG. 211, DIG. 212, DIG. 213, DIG. 214

[56] References Cited

U.S. PATENT DOCUMENTS

| 3,804,680 | 4/1974 | Martin et al. | 148/162 |
| 4,622,200 | 11/1986 | Gold et al. | 376/159 |
| 4,729,866 | 3/1988 | Ruddy et al. | 376/153 |
| 4,801,421 | 1/1989 | Ackerson et al. | 376/249 |
| 4,852,397 | 8/1989 | Haggag | 73/82 |
| 5,130,081 | 7/1992 | Niedrack | 376/305 |

FOREIGN PATENT DOCUMENTS

| 0287501 | 3/1988 | European Pat. Off. . |
| 0308888 | 9/1988 | European Pat. Off. . |
| 0312247 | 10/1988 | European Pat. Off. . |
| 2208000 | 7/1988 | United Kingdom . |

OTHER PUBLICATIONS

International Atomic Energy Agency—International Symposium on Safety Aspects of the Ageing and Maintenance of Nuclear Power Plants, Vienna, Austria, Jun. 29–Jul. 3, 1987 IAEA-SM-295 "For BWR longevity, plants are the best teachers" R. J. Brandon, P. P. Stancavage General Electric Company.

Primary Examiner—Donald P. Walsh
Assistant Examiner—Meena Chelliah
Attorney, Agent, or Firm—Antonelli, Terry, Stout & Kraus

[57] ABSTRACT

A method and an apparatus for estimating the remaining service life of an object by measuring the physical quantity of a sample and which are applicable to a nuclear reactor. A plurality of model samples are experimentally prepared by preliminarily disposing a material having substantially the same composition as the object to be subjected to the estimation in an environment substantially the same as the object and measuring the physical quantities of the model samples in relation with exposure times. From this experiment, a relationship between the exposure time and the physical quantity under such an environment is obtained. Further, a critical exposure time which will cause an unstable fracture of a material of an actual sample, which is made of a material substantially the same as the object and placed in substantially the same environment as the object, is preliminarily obtained from the relationship between the exposure time and the physical quantity for the model samples. The physical quantity of the actual sample is then measured. Subsequently, an actual exposure time corresponding to the physical quantity of the actual sample is obtained by using the relationship between the physical quantity and the exposure time. Thereafter, a difference between the critical exposure time and the actual exposure time is calculated to obtain a remaining service life of the object.

35 Claims, 19 Drawing Sheets

PREDICTABLE RANGE OF REMAINING SERVICE LIFE

PREDICTABLE RANGE OF
REMAINING SERVICE LIFE

STRESS INTENSITY FACTOR $K = F\sigma \sqrt{a} = F \cdot \frac{P}{WB} \cdot \sqrt{a}$

METHOD OF AND APPARATUS FOR ESTIMATING REMAINING SERVICE LIFE OF MATERIAL BEING EXPOSED TO RADIANT RAY IRRADIATION

BACKGROUND OF THE INVENTION

1. Field of the Invention

The present invention relates to a method and an apparatus for estimating the remaining service life of a material and more particularly, to a remaining service life prediction method and apparatus well suited for application to a metal material which is used in high-temperature water and under neutron irradiation and which undergoes stress corrosion cracking.

2. Description of the Related Art

Since a material such as austenitic stainless steel used in a nuclear reactor is subjected to irradiation with radioactive rays in a corrosive environment of high-temperature water, it may possibly undergo irradiation-assisted stress corrosion cracking (IASCC) ascribable to corrosion damage or deterioration in the material. The IASCC is classified into the transgranular type and the intergranular type, depending upon the form of a fracture surface developed.

If an accident should take place in such a nuclear reactor plant, it will have very serious consequences. It is accordingly imperative that any accident is prevented from occurring. As a process for suppressing the IASCC, hydrogen injection has been presently proposed. With this process, the material is doped with hydrogen, thereby reducing a dissolved oxygen concentration or lowering corrosion potential.

In addition, the safety of the material from the stress corrosion cracking has heretofore been ensured by making an annual routine inspection to verify the use thereof since the last routine inspection. With this method, the safety at the time of the inspection can be checked, but the service life of the material cannot be predicted as to whether the stress corrosion cracking will arise before the next routine inspection.

Additionally, a service life diagnostic system for a metal material concerning the stress corrosion cracking is disclosed in the official gazette of Japanese Patent Application Laid-open No. 69942/1989. This technique consists in that the stress corrosion cracking characteristic of the material is evaluated by obtaining the quantity of charges versus the active dissolution of a fresh metal surface and the localization factor of corrosion.

With the aforementioned technique, in estimating the remaining service life of a sample, the quantity of charges versus the active dissolution of the fresh metal surface and the localization factor of the corrosion must be obtained. This method has the problem that the remaining service life of the material which becomes brittle due to the irradiation with particles cannot be estimated merely by subjecting the sample to a simple test.

SUMMARY OF THE INVENTION

An object of the present invention is to provide a remaining service life prediction apparatus and method applicable to a nuclear reactor, which is capable of estimating the remaining service life of a part to-be-monitored by measuring the characteristics of a sample with ease.

One aspect of the present invention features a method for estimating a remaining service life of an object which is placed in an environment subjected to exposure to high-energy radiant ray and made of a material which will deteriorate in mechanical properties under the exposure to high-energy radiant ray. The method comprises a first step of subjecting a material having substantially the same composition as the object to exposure to the high-energy radiant ray under a plurality of exposure conditions to prepare a plurality of model samples, and physical quantities of the respective model samples, indicative of the mechanical properties of the respective samples, are obtained in relation to exposure times to the respective model samples to obtain a relationship between an exposure time and a physical quantity for said object; a second step for obtaining a critical exposure period of time which will cause unstable fracture in the material of the object from the relationship obtained in the first step; a third step of placing an actual sample of a material having substantially the same composition as the model samples in the environment where the object is placed and subjected to exposure to the high-energy radiant ray; a fourth step for measuring a physical quantity of the actual sample after the exposure to the high-energy radiant ray; a fifth step for obtaining an actual exposure time corresponding to the measured physical quantity of the actual sample obtained in the fourth step on the basis of the relationship between the physical quantity and the exposure time obtained in the first step with regard to the actual exposure time thus obtained as an actual exposure time of the object; and a sixth step for obtaining a difference between the critical exposure time obtained in the second step and the actual exposure time of the object obtained in the fourth step.

The first step preferably includes a first-first step for obtaining a relationship between the physical quantities of the model samples and exposure doses applied thereto, and a first-second step for obtaining a relationship between exposure doses and exposure times corresponding to the respective exposure doses for the object. The first-second step, preferably, includes a second-first step for obtaining a critical value of the physical quantity which will cause unstable fracture in the material from the relationship obtained in the first-first step and a critical exposure dose corresponding to the critical value of the physical quantity, and a second-second step for obtaining a critical exposure time for the object corresponding to the critical exposure dose from the relationship between the exposure doses and the exposure times obtained in the first-second step.

Another aspect of the present invention features an apparatus for estimating a remaining service life of an object which is placed in an environment subjected to exposure to high-energy radiant ray and made of a material which will deteriorate in mechanical properties under the exposure to high-energy radiant ray, with the apparatus comprising a first storage means for storing a relationship between an exposure time and a physical quantity for the object which has been obtained by preparing a plurality of model samples made of a material having substantially the same composition as the object and subjected to exposure to the high-energy radiant ray under a plurality of exposure conditions and by obtaining physical quantities of the respective model samples, indicative of the mechanical properties of the respective samples, in relation to exposure times to the respective model samples; a first computing means for obtaining a critical exposure period of time which will cause unstable fracture in the material of the object from the relationship stored in the first storage means; a taking-in means for taking in a physical quantity of an actual sample made of a material having substantially the same composition as the model samples and placed in the environment where the object is placed and subjected to exposure to the high-energy radiant ray, which is obtained after the exposure to the high-energy radiant ray; means for obtaining an actual exposure time corresponding to the physical quantity of the actual sample taken in by the taking-in means on the basis of the relationship between the physical quantity and the exposure time stored in the first storage means to regard the actual exposure time thus obtained as an actual exposure time of the object and for obtaining a difference between the critical exposure time obtained by the first computing means and the actual exposure time of the object.

The first storage means preferably includes a first-first storage means for storing a relationship between the physical quantities of the model samples and exposure doses applied thereto, and a first-second storage means for storing a relationship between exposure doses and exposure times corresponding to the respective exposure doses for the object. The second storage means preferably includes a second-first storage for storing a critical value of the physical quantity which will cause unstable fracture in the material from the relationship stored in the first-first storage means and a critical exposure dose corresponding to the critical value of the physical quantity, and a second-second storage means for storing a critical exposure time for the object corresponding to the critical exposure dose from the relationship between the exposure doses and the exposure times stored in the first-second storage means.

As mentioned above, the actual sample employable in the first aspect of the present invention is made of a material having substantially the same material as the object to be subjected to the estimation and placed in an environment subjected to exposure to a high-energy radiant ray substantially the same as the object. The term "high-energy radiant ray" is used herein to include a high-energy particle such as neutron, ion, alpha ray or gamma ray, and further include electromagnetic wave. A plurality of model samples are experimentally prepared by preliminarily disposing a material having substantially the same composition as the object to be subjected to the estimation in an environment substantially the same as the object and measuring physical quantities of the model samples in relation with exposure times. From this experiment, a relationship between the exposure time and the physical quantity under such an environment is obtained. Further, a critical exposure time which will cause an unstable fracture of the material of the actual sample is preliminarily obtained from the relationship between the exposure time and the physical quantity for the model samples. The unstable fracture includes a brittle fracture and a ductile fracture.

The physical quantity of the actual sample placed in an environment substantially the same as the environment to which the object is to be subjected to the estimation, is then measured. Subsequently, an actual exposure time corresponding to the physical quantity of the actual sample is obtained by using the relationship between the physical quantity and the exposure time. Thereafter, a difference between the critical exposure time and the actual exposure time is calculated to obtain a remaining service life of the object.

The physical quantity may be in the form of a mechanical property such as a compliance, a hardness, a strength or an elongation, or a stress corrosion cracking.

The method and apparatus for estimating a remaining service life of an object according to the present invention is suitably employable for estimation of a material of an inner structure of a fusion reactor, nuclear reactor or a cyclotron.

BRIEF DESCRIPTION OF THE DRAWINGS

FIG. 18 is a graphical illustration of a relationship between the load P applied to a sample and the displacement Φ of the outer opening of a notch formed in the sample, obtained from test pieces of unequal crack lengths a;

PREFERRED EMBODIMENTS OF THE INVENTION

Figure 14:
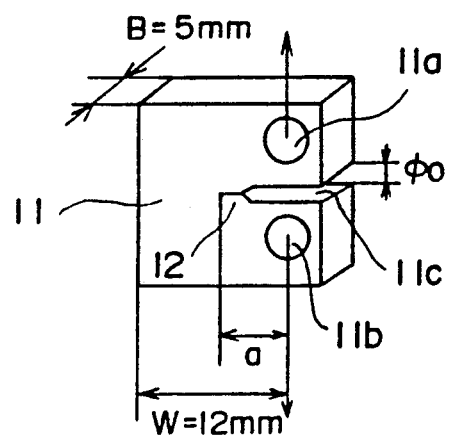
FIG. 14 is a perspective view of a sample constructed in accordance with the present invention.
Figure 17:
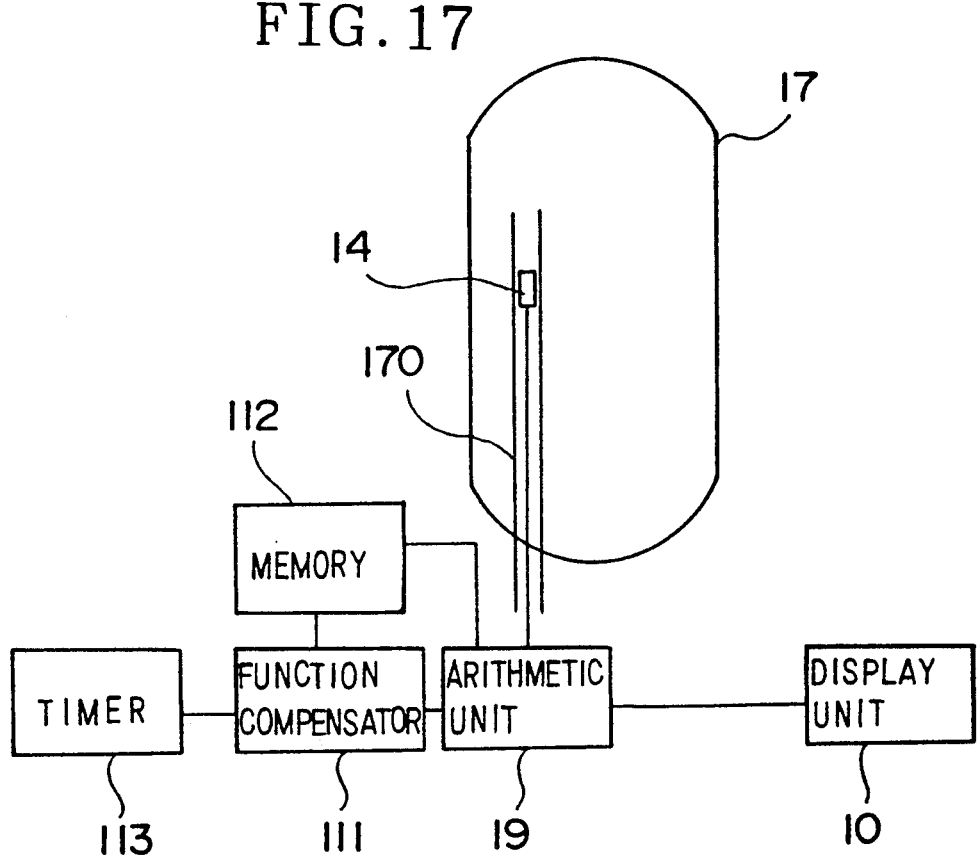
FIG. 17 is a schematic block diagram showing the constitution of a remaining service life prediction apparatus according to the present invention.

As shown in FIG. 17, an apparatus for estimating the remaining service life of austenitic stainless steel which is the constituent material of a nuclear reactor, includes a measuring device 14 for measuring the compliance $\lambda$ of a sample 11 shown in FIG. 14 in terms of a physical quantity, a memory 112 for storing therein a function g which expresses the relationship between the compliance $\lambda$ of the sample 11 and an elapsed time t and which has been experimentally obtained beforehand, as well as an elapsed time $t_c$ at which the service life of the sample 11 will expire and which has also been experimentally obtained beforehand, and an arithmetic unit 19 for calculating the remaining service life with the measured result of the measuring device 14 and the stored contents of the memory 112. Further, the prediction apparatus includes a display unit 10 for displaying the remaining service life, a function compensator 111 for compensating the function g stored in the memory 112, and a timer 113 for generating an elapsed time $t_o$ for use in the compensation. In embodiment of FIG. 17, the elapsed time t corresponds to the exposure time as mentioned above, and the elapsed time $t_c$ at which the service life of the sample will expire corresponds to the critical exposure time at which the unstable fracture will be caused as mentioned above.

Figure 15:
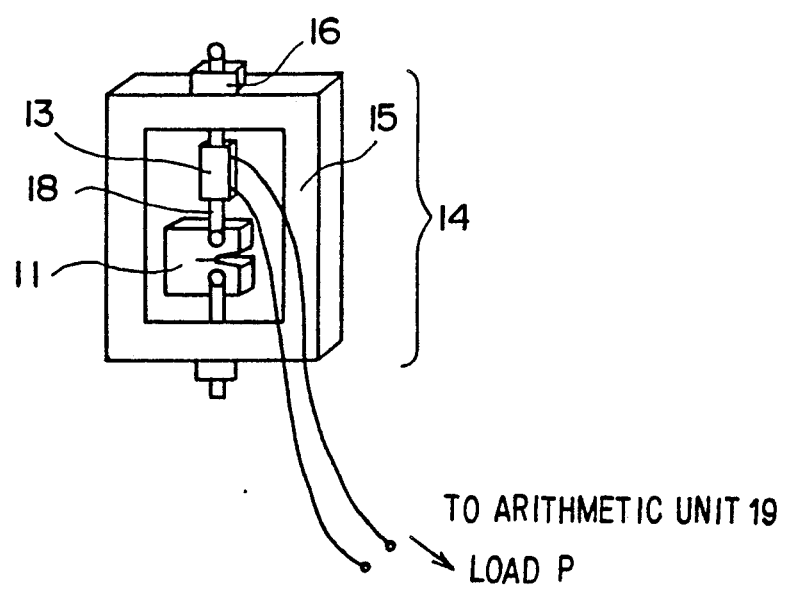
FIG. 15 is a perspective view of a measuring device according to the present invention.

As illustrated in FIG. 15, the measuring device 14 in which the sample 11 is set includes a tension jig 18 connected to the sample 11 for drawing this sample, and a screw 16 for fixing the tension jig 18 to a constraint jig 15 in the state in which a predetermined displacement $\Phi$ is given to the sample 11. Mounted on the tension jig 18 is a load cell 13 which measures a tensile load P acting on the sample 11 and then tranduces the measured tensile load P into an electric signal. In an example, the load cell 13 employed was one rated at a maximum allowable load of 500 kg. and an accuracy of ±1 kg., which was usable in high-temperature and high-pressure water of at most 370° C. and at most 150 atm. irradiated with radiant ray.

In the present embodiment, the sample 11 is used either as the model sample or as the actual sample. The sample 11 is made of austenitic stainless steel having the same composition as that of the constituent material of the nuclear reactor 17 to have the service life estimated. As shown in FIG. 14, the sample 11 has the dimensions of a thickness B of about 5 mm and a width W of about 12 mm, and it is formed with through holes 11a and 11b for connecting the sample 11 to the tension jig 18. Also, a notch 11c whose outer opening has a width $\Phi_o$ under no load is provided between the through holes 11a and 11b. Besides, a crack 12 having a length of about 1.5 mm is provided at the inner tip of the notch 11c by preliminarily fatiguing the sample 11. By way of example, the fatigue pre-crack 12 was provided on the basis of the rating (ASTM E-399) in such a manner that the through holes 11a and 11b of the sample 11 were connected to a tension tester, and that the sample 11 was drawn in the directions of arrows in FIG. 14 in atmosphere of room temperature with a stress intensity factor value which was not greater than 60% of the fracture toughness of the material of this sample. Thus, the innermost end of the fatigue pre-crack 12 reached a position of about ½ of the width W of the sample 11. The fatigue pre-crack 12 is formed in each of the samples 11 which are to be used as the model sample and the actual sample.

The sample 11 formed with the fatigue pre-crack 12 is directly connected to the tension jig 18 having the built-in load cell 13, and it is drawn by the tension tester until the outer opening displacement of the notch 11c becomes the predetermined displacement $\Phi$. In this state, the tension jig 18 is fixed to the constraint jig 15 by the screw 16. Thus, the sample 11 is set in the measuring device 14.

Figure 16:
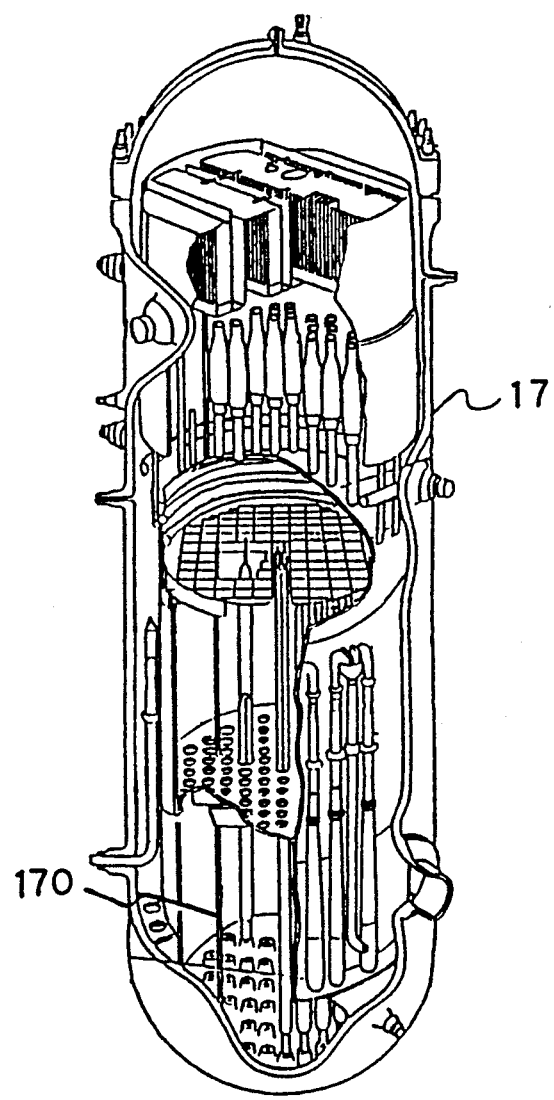
FIG. 16 is a partially-cutaway perspective view of a construction of a nuclear reactor to which the embodiment of FIG. 14 is applied.

As illustrated in FIGS. 16 and 17, the measuring device 14 with the sample 11 mounted thereon as the actual sample is disposed in a neutron monitoring tube 170 within the nuclear reactor 17. In this embodiment, the measuring device 14 is inserted in the nuclear reactor 17 at the beginning of the operation thereof. The wall thickness of the neutron monitoring tube 170 is about 1.5 mm, and is sufficiently small when compared with about 10 odd cm which is the metal penetrating power of the neutron irradiation. Therefore, neutron irradiation in the monitoring tube 170 is hardly any different from direct irradiation, and the sample 11 set in the measuring device 14 is substantially in the same environment as that of the constituent material of the nuclear reactor 17. The signal lines of the load cell 13 shown in FIG. 15 are extended inside the neutron monitoring tube 170 and led out of the nuclear reactor 17, and are connected to the arithmetic unit 19.

Figure 19:
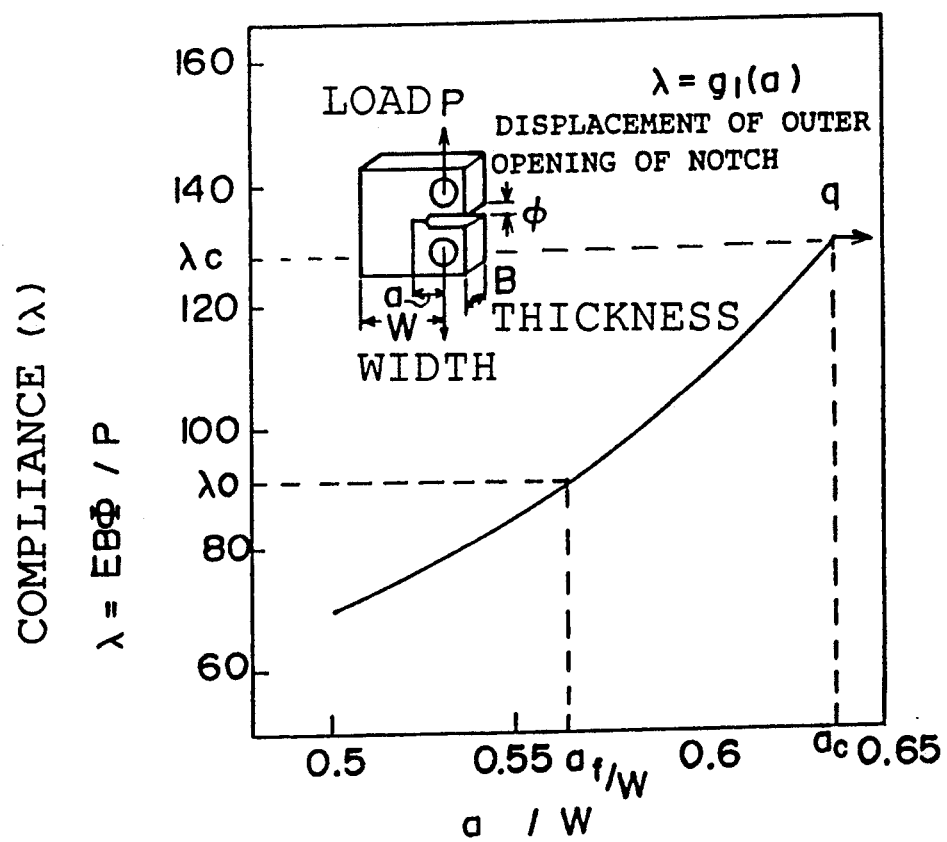
FIG. 19 is a graphical illustration of a relationship between the crack length a and the compliance $\lambda (= E B \Phi /P$ where E: Young's modulus, and B: sample thickness) of a sample arranged in an environment simulative of a nuclear reactor.
Figure 20:
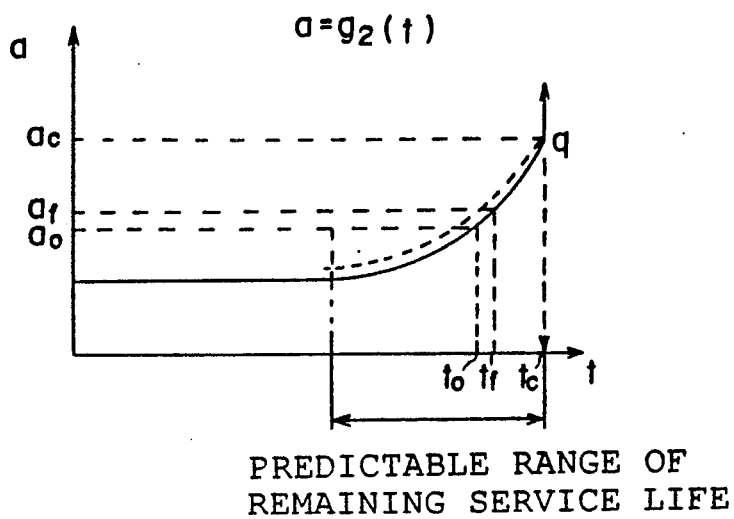
FIG. 20 is a graphical illustration of a relationship between the lapse of time t and the crack length a in the environment simulative of the nuclear reactor.
Figure 23:
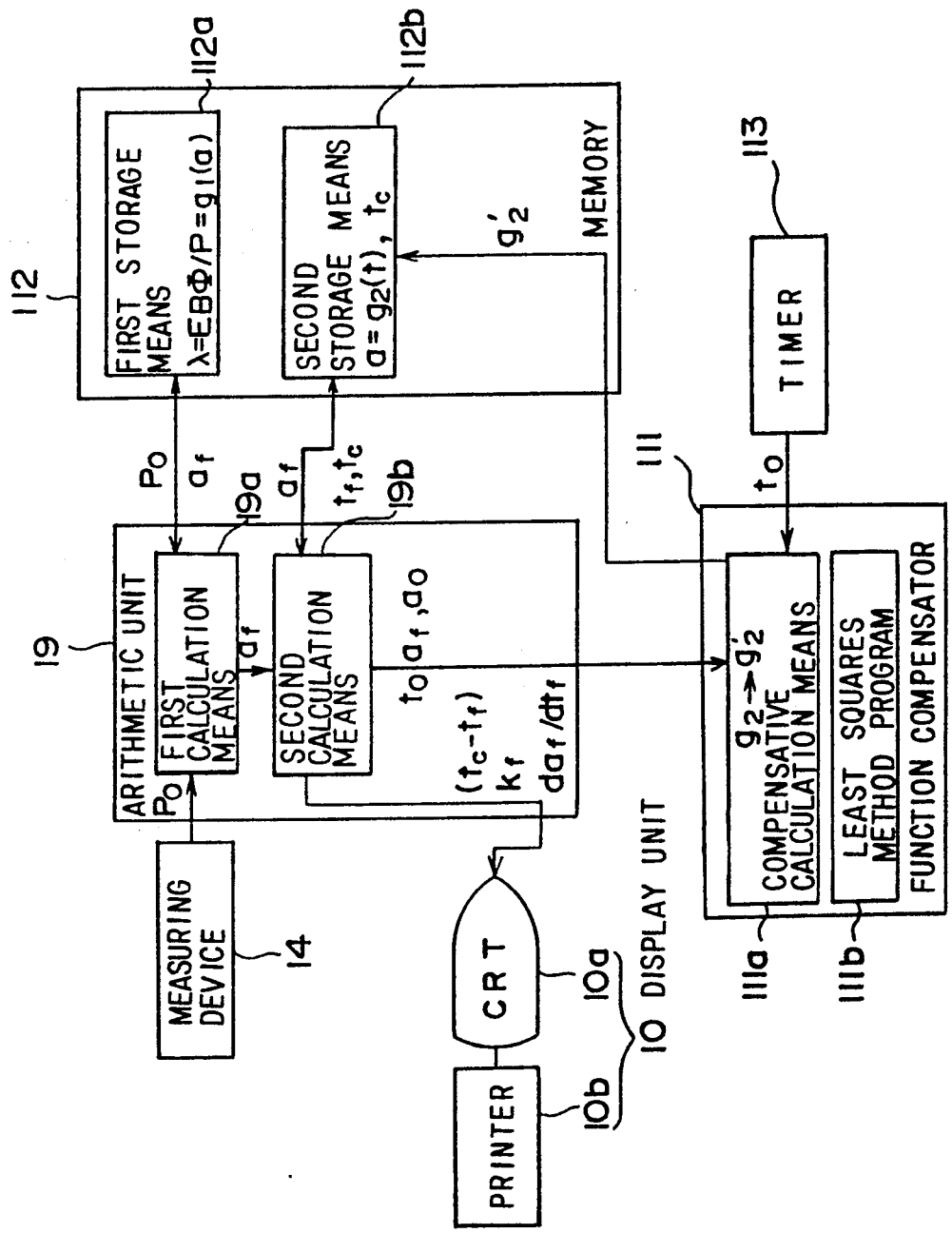
FIG. 23 is a block diagram showing the construction of an embodiment of the present invention.

As shown in FIG. 23, the memory 112 includes first storage means 112a and second storage means 112b. The first storage means 112a stores therein the formula of the function $\lambda = g1(a)$ which represents the relationship between the compliance $\lambda$ of the sample 11 and the crack length a thereof and which has been experimentally obtained beforehand. The graph of the function $\lambda = g1(a)$ is depicted in FIG. 19. On the other hand, the second storage means 112b stores therein the formula of the function $a = g2(t)$ which represents the relationship between the crack length a of the sample 11 and the elapsed time t since the arrangement of the measuring device 14 in the nuclear reactor 17 and which has also been experimentally obtained beforehand, and the time $t_c$ at which the service life of the sample 11 will expire due to an unstable fracture caused on the material, austenitic stainless steel. The graphs of the function $a = g2(t)$ and the life time $t_c$ are depicted in FIG. 20.

The functions g1 and g2 and the service life time $t_c$ were in the following manner. The measuring device 14 with the sample 11 mounted thereon as the model sample was arranged in a reactor simulation environment (high-temperature and high-pressure water of 288° C.

and 80 atm. irradiated with Gamma-ray of $10^5 \sim 10^8$ R/H) prepared experimentally, whereupon the elapsed time t since the arrangement, the compliance λ and the crack length a were measured. In this environment, the crack 12, preliminarily formed, lengthened slowly and stably with the elapsed time t, and the length a thereof enlarged gradually. The crack length a was measured by actually confirming the innermost end of the crack 12 with a microscope every predetermined elapsed time period.

Figure 18:
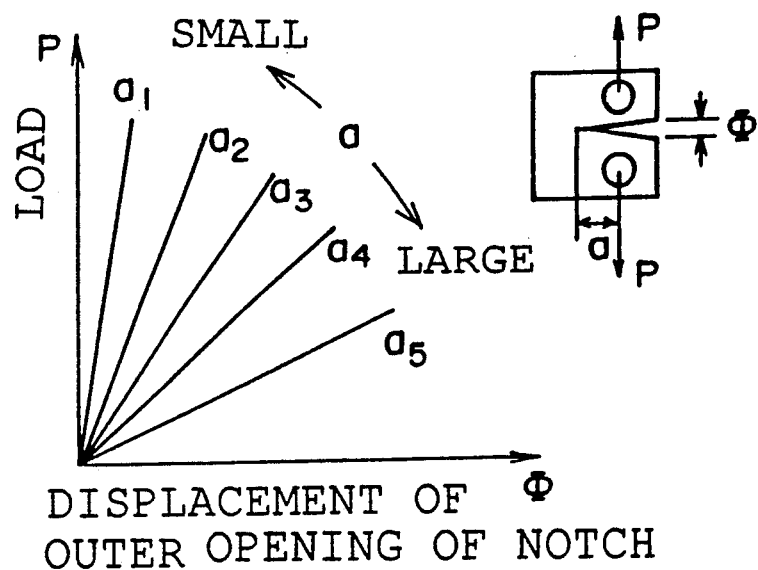

In addition, the compliance λ of the sample 11 was measured as described below. The compliance λ is given by λ=E B Φ/P (where E=Young's modulus, and B=thickness of the sample 11). FIG. 18 illustrates the relationships between the load P and the displacement Φ of the outer opening of the notch 11c within the elasticity limits of each sample 11, which were obtained for five samples 11 having unequal crack lengths a ($a_1 \sim a_5$ in the figure). It is seen from FIG. 18 that the gradient of a straight line indicative of the displacement Φ decreases as the crack length enlarges. The compliance λ is a value obtained in such a manner that the inverse number (F/P) of the gradient in FIG. 18 is multiplied by the Young's modulus E and the thickness B of the test piece 11, and that the resulting product is normalized. With the measuring device 14 in this embodiment, the opening displacement of the sample 11 is held at the predetermined value Φ, and the load P acting on the sample 11 at this time is obtained in the form of the output load P of the load cell 13. Accordingly, the displacement Φ was given as a constant, and the compliance λ was evaluated by measuring only the load P. The compliance λ and the crack length a were graphically illustrated as in FIG. 19. Thus, the formula representative of the function λ=g1(a) has been obtained. It is seen from FIG. 19 that, as the crack length a increases, the load P decreases, so the compliance λ increases.

Besides, the elapsed time t was separately measured, and the relationship thereof with the corresponding crack length a was graphically illustrated as in FIG. 20. Thus, the formula representative of the function a=g2(t) has been obtained. At the point of time q at which the crack length a has increased to the stress intensity factor value K and fracture toughness value Kic of the material of the sample 11, the crack 12 stretches rapidly, and the sample 11 fails. The experiment in the reactor simulation environment was continued until the unstable fracture of the sample 11 as the model sample occurs, and the elapsed time $t_c$ expended until the failure time point q was measured. This elapsed time $t_c$ has been set as the elapsed time $t_c$ at which the service life of the sample 11 will expire.

These data items are stored in the memory 112. The functions g1 and g2 are stored in the forms of the formulae g1=k1 $a^5$+k2 $a^4$+k3 $a^3$+k4 $a^2$+k5 a+k6 (where k1~k6 denote constants) and g2=m1 $t^5$+m2 $t^4$+m3 $t^3$+m4 $t^2$+m5 t+m6 (where m1~m6 denote constants) obtained by reading FIGS. 19 and 20, respectively. Besides, the measurement detection limits of the crack length a were ±0.01 mm. Herein, since the length of the fatigue pre-crack 12 was ¼·W=6 mm, the values of the crack length a less than 6.02 mm fell within the detection limits. Thus, the predictable range of the remaining service life becomes as indicated in FIG. 20.

As shown in FIG. 23, the arithmetic unit 19 includes first calculation means 19a and second calculation means 19b. The first calculation means 19a is loaded with the function g1 of the first storage means 112a, and substitutes the measured load Po of the measurement means 14 with the actual sample mounted thereon into the function g1. A crack length $a_f$ corresponding to the load Po is evaluated in accordance with $\lambda_0$=E B Φ/Po=g1($a_f$) thus obtained, and it is output to the second calculation means 19b. This second calculation means 19b is loaded with the function g2 of the second storage means 112b, and substitutes the input crack length $a_f$ from the first calculation means 19b into the function g2. An elapsed time $t_f$ corresponding to the crack length $a_f$ is evaluated in accordance with $a_f$=g2($t_f$) thus obtained. Further, the second calculation means 19b is loaded with the elapsed time $t_c$ until the expiration of the service life, from the second storage means 112b, and the second calculation means 19b computes the remaining service life ($t_c - t_f$), which is output to the display unit 10. Still further, the second calculation means 19b computes from the data $a_f$ obtained before, the change rate $da_f/dt_f$ of the crack length $a_f$ and the stress intensity factor K=f σ√a=f·Po/W B·√a (where f: form factor given beforehand, s: stress, and a: crack length), and it transfers the computed results to the display unit 10.

The function compensator 111 includes a compensative calculation means 111a, and a program storage portion 111b storing a least squares method program therein. The compensative calculation means 111a of the function compensator 111 receives a time $t_o$ at the measurement of the load Po corresponding to the crack length $a_f$, from the timer 113, and it causes the second calculation means 19b to compute a crack length $a_o$ corresponding to the time $t_o$ in accordance with the function g2. Thereafter, the means 111a of the function compensator 111 compares the crack length values $a_f$ and $a_o$ in the set ($a_f$, $t_f$) obtained in accordance with the function a=g2(t) and the set ($a_o$, $t_o$) calculated backward from the actual time lapse $t_o$. In a case where the difference between the values $a_f$ and $a_o$ is greater than a preset value, the means 111a is loaded with the least squares method program from the program storage portion 111b. Subsequently, using the set of data ($a_c$, $t_c$) and a plurality of sets of data ($a_{fn}$, $t_{on}$) (where n: number indicating the sequence of the data) obtained up to that point, the compensative calculation means 111a applies fitting to the function g2 on the basis of the least squares method and compensates this function g2 to derive a different function $a_f$=g2'($t_o$). The use of the set ($a_c$, $t_c$) is intended to fix the crack length $a_c$=g2($t_c$) corresponding to the life time $t_c$ in order that the function g2' may satisfy $a_c$=g2'($t_c$).

In addition, the display unit 10 includes a CRT 10a and a printer 10b. The CRT 10a displays the remaining service life ($t_c - t_f$), the stress intensity factor K and the change rate $da_f/dt_f$ of the crack length $a_f$. The printer 10b prints out these data items on sheets of paper.

Figure 22:
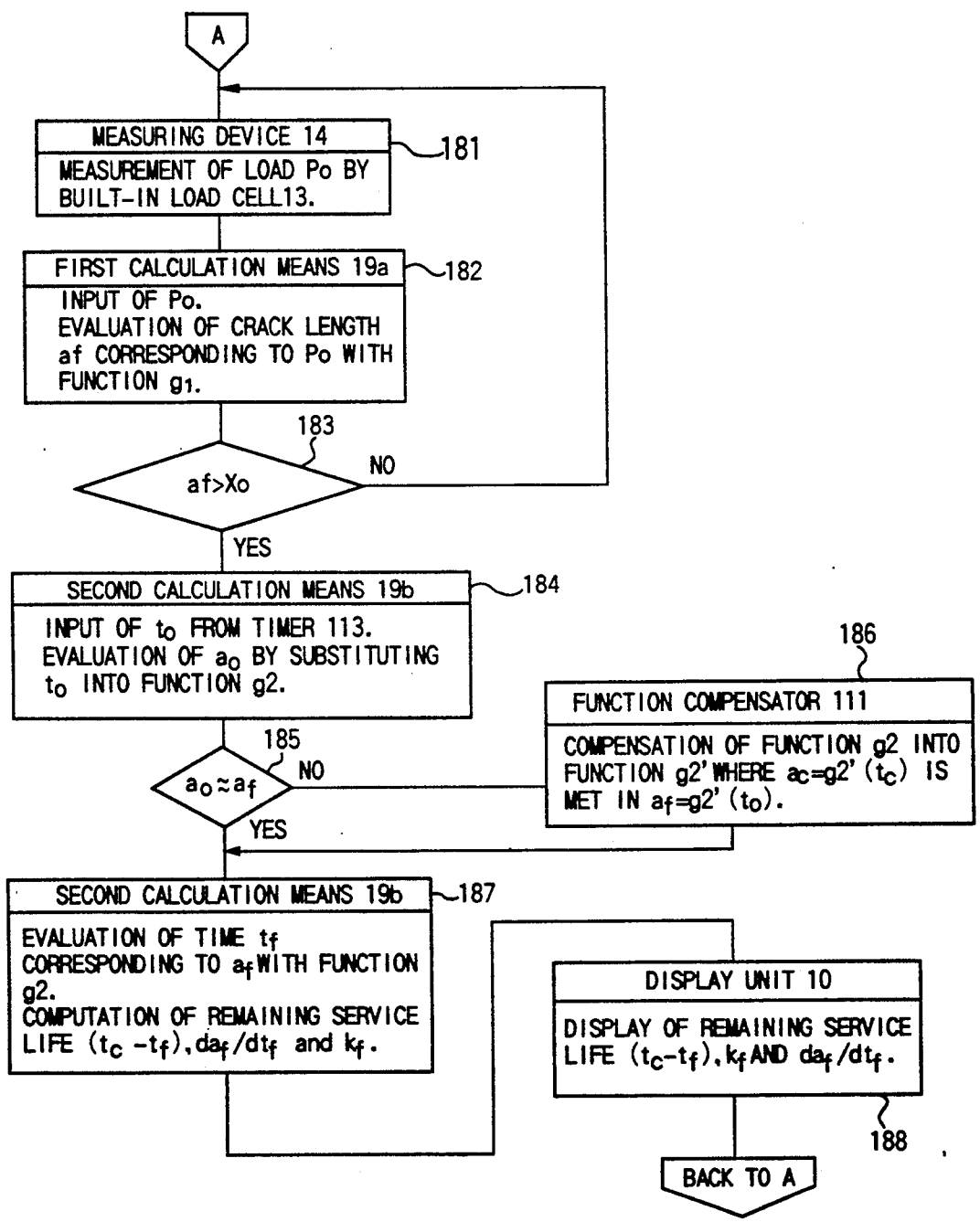
FIG. 22 is a flow chart showing the operation of service life prediction based on the remaining service life prediction apparatus of the invention.

Next, the operation of the apparatus of this embodiment for estimating the remaining service life of the austenitic stainless steel which is the constituent material of the nuclear reactor will be described with reference to the flow chart of FIG. 22.

The measuring device 14 measures the load Po acting on the sample 11 as the actual sample by the load cell 13, and transfers the signal of this load to the arithmetic unit 19 (step 181). The first calculation means 19a of the arithmetic unit 19 receives the signal of the load Po, and evaluates the crack length $a_f$ corresponding to the load Po with the function g1 of the first storage means 112a of the memory 112 (step 182). Herein, when the crack length $a_f$ is greater than the detection limit value $X_o = 0.02$ mm mentioned before, the first calculation means 19a transfers the signal of the crack length $a_f$ to the second calculation means 19b, and when it is not transferred, the routine returns to the step 181 (step 183).

The compensative calculation means 111a of the function compensator 111 receives the signal of the time $t_o$ at the measurement of the load Po corresponding to the crack length $a_f$ from the timer 113, and transfers it to the second calculation means 19b of the arithmetic unit 19 so as to compute the crack length $a_o$ corresponding to the time $t_o$ in accordance with the function g2 (step 184). The calculation means 111a of the function compensator 111 compares the crack length values $a_f$ and $a_o$ (step 185). Herein, when the difference of these values is greater than the preset value, the calculation means 111a compensates the function g2 to produce the function g2' with the least squares method as stated before (step 186). The second calculation means 19b evaluates the time $t_f$ corresponding to the crack length $a_f$ in accordance with the compensated function g2 stored in the second storage means 112b. Further, the means 19b computes ($t_c - t_f$) from the life-expiration elapsed time $t_c$ stored in the second storage means 112b, and it transfers the result to the display unit 10 as the remaining service life. Still further, the means 19b computes the change rate $da_f/dt_f$ of the crack length $a_f$ and the stress intensity factor $K_f = F\;s\sqrt{a_f} = F \cdot Po/W\;B \cdot \sqrt{a_f}$ (where F: form factor, and s: stress) corresponding to the crack length $a_f$, from the data obtained until then, and it transfers the computed results to the display unit 10 (step 187). The display unit 10 displays the remaining service life ($t_c - t_f$), the stress intensity factor $K_f$ and the change rate $da_f/dt_f$ (step 188).

Figure 21:
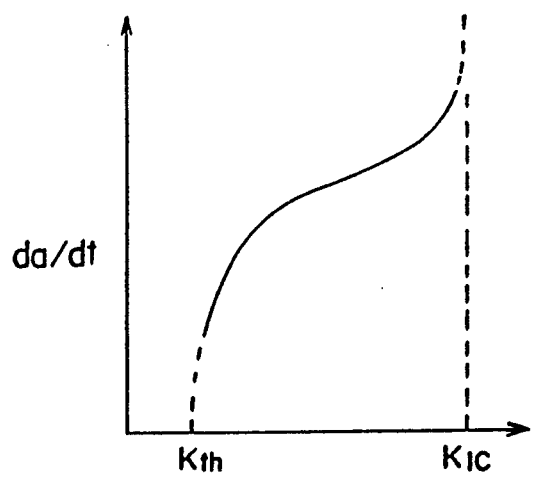
FIG. 21 is a graphical illustration of a relationship between the stress intensity factor K and the crack growth rate da/dt of a sample in the environment simulative of the nuclear reactor.

In this manner, according to the remaining service life prediction apparatus of this embodiment, the remaining service life of the austenitic stainless steel which is the constituent material of the nuclear reactor can be easily and accurately estimated using the simple construction whereby the sample 11 (actual sample) provided with the crack 12 beforehand is arranged in substantially the same environment as that of the constituent material within the nuclear reactor and that the load on the sample 11 is measured. Usually, any structure is used in a stress condition in which no crack appears or grows (namely, in a stress condition in which the stress intensity factor K is smaller than a cracking threshold value Kth indicated in FIG. 21), but a crack can appear and grow originating from a welding defect, an inclusion or the like. The crack having appeared grows slowly and stably with time. However, when the length of the crack increases to render the value of the factor K equal to the known fracture toughness value Kic of the material, the crack stretches rapidly and fails as illustrated in FIGS. 20 and 21. The remaining service life prediction apparatus of this embodiment induces such cracking in the sample 11 as the actual sample under the environment within the actual reactor and simulates it with the mechanical characteristic values of the sample 11, thereby estimating the remaining service life of the constituent material with accuracy.

Moreover, according to the present invention, the compliance λ of the sample 11 is set as a variable, and it is measured by the measuring device 14 which affords the predetermined displacement Φ to the sample 11. This makes it sufficient to merely measure the load P acting on the sample 11, and realizes the actual measurement in the interior of the nuclear reactor under severe environmental conditions. Furthermore, when the evaluated crack length is greatly different from the value actually measured, the function g2 which is the known crack advance curve is corrected by the function compensator 111. This enables a highly accurate prediction of the service life. Besides, in the above, there has been described the operation in which the function compensator 111 executes the steps 184 thru 186 in FIG. 22 every cycle of the prediction. However, these steps need not always be executed every cycle of the prediction, but the apparatus can, of course, be constructed so as to execute the steps 184 thru 186 only once in several cycles.

In the present invention, the crack length a actually measured and the crack advance rate $da_f/dt_f$ as well as the stress intensity factor K calculated by the service life prediction apparatus are displayed on the display unit such as CRT or printer, so that the behavior of the crack growth of the material within the reactor can be checked at a glance. Accordingly, the remaining service life prediction apparatus is very convenient.

Besides, in the first embodiment, the function to be stored in the memory 112 is separated into the functions $\lambda = g1(a)$ and $a = g2(t)$, which are formed by measuring the values of the crack length a once. Here, $\lambda = g1 \cdot g2(t) = g(t)$ holds. Therefore, it is of course possible to directly evaluate the remaining service life from the elapsed time t in accordance with the single function g.

Further, in this embodiment, the sample 11 employed has the same composition as that of the reactor part whose service life is to be monitored. However, if the relationship between secular changes in the mechanical characteristics of the part to be monitored and the sample 11 is known beforehand, the sample 11 can alternatively be formed of a material of different composition. Also, in this embodiment, the measuring device 14 is arranged in the neutron monitoring tube 170. However, even a reactor part located in an environment different from the environment in the vicinity of the neutron monitoring tube 170 can have its service life monitored as long as the difference of the remaining service life based on the different environment is known. In any of these cases, a resulting value is corrected by calculation means on the basis of the difference of the remaining service life.

Although the model sample employed in the present embodiment is substantially the same in configuration as the actual sample in the present embodiment, it is not limited to such a configuration. Any other configurations may be employable so long as it can assures that a relationship between the exposure time and the compliance λ is obtained.

Figure 1:
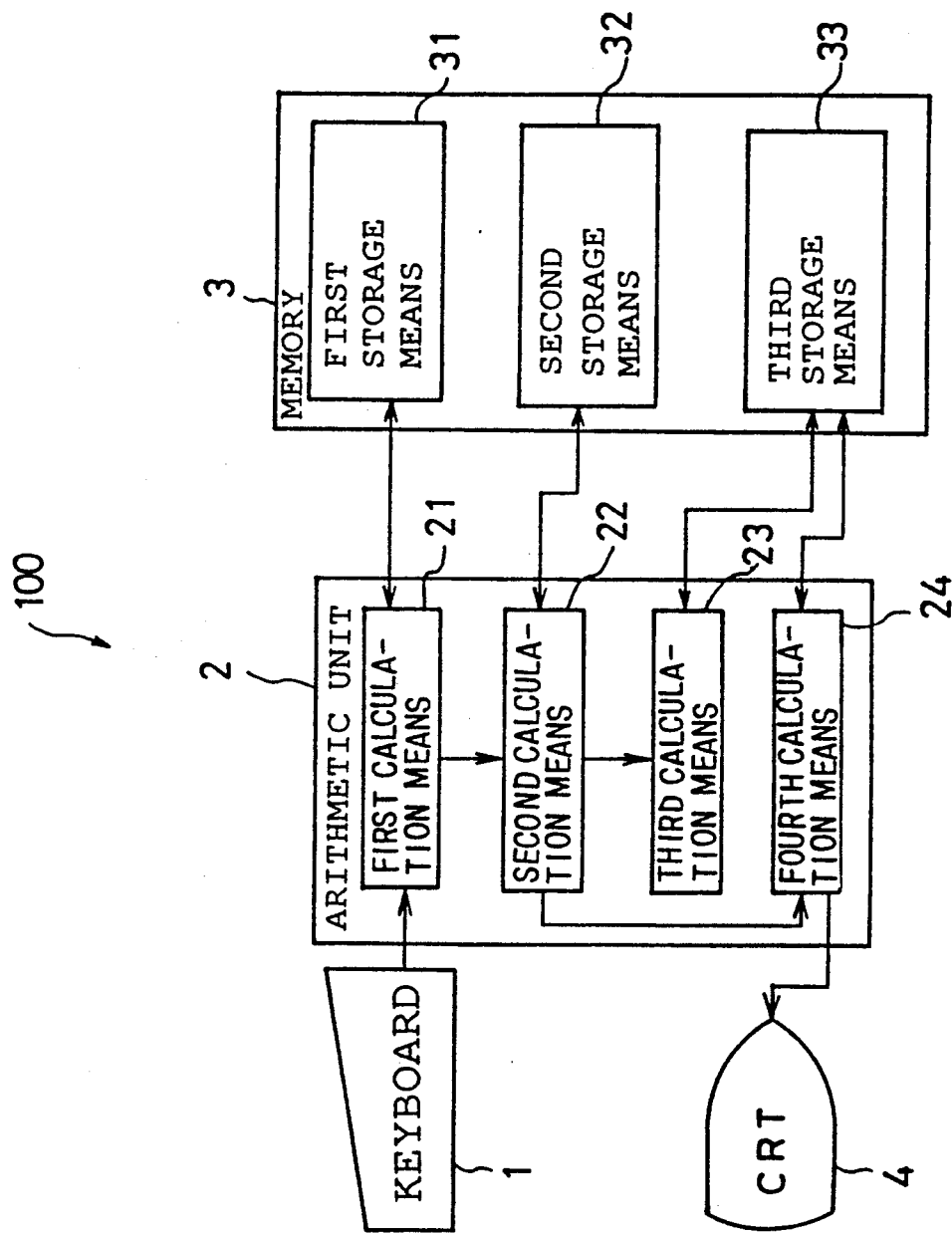
FIG. 1 is a block diagram of a remaining service life prediction apparatus according to an embodiment of the present invention.

As illustrated in FIG. 1, in accordance with a second embodiment of the present invention, the remaining service life prediction apparatus 100 comprises input means such as a keyboard 1 through which a change in the mechanical characteristic value of an actual sample irradiated with particles such as neutrons is received, a memory 3 in which predetermined information items are stored beforehand, an arithmetic unit 2 which executes predetermined calculations in accordance with programs written in a memory not shown, and output means such as a CRT 4 which displays a remaining service life transferred from the arithmetic unit 2.

The memory 3 includes first storage means 31 for previously storing therein the relationship between a change in the mechanical characteristic value of a model sample irradiated with the particles of predetermined dose and a radiation embrittlement percentage indicating the degree of embrittlement of the model sample attributed to the particle ray irradiation, second storage means 32 for preliminarily storing therein the relationship between the particle exposure of the model sample and the radiation embrittlement percentage thereof, as well as a critical exposure corresponding to the critical radiation embrittlement percentage at which the model sample breaks, and third storage means 33 for preliminarily storing therein the relationship between the particle exposure of the actual sample having substantially the same composition as that of the model sample and the particle ray irradiation term of the actual sample.

Figure 3A:
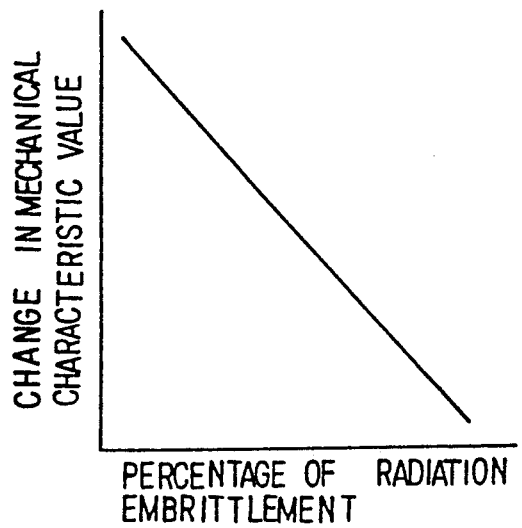
FIGS. 3(a)~3(c) are graphical illustrations of contents of a memory in the remaining service life prediction apparatus of the embodiment of FIG. 1.
Figure 3B:
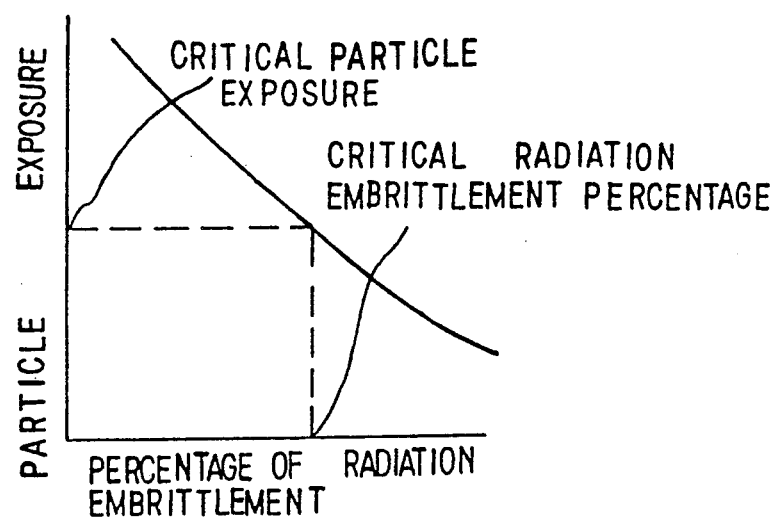
Figure 3C:
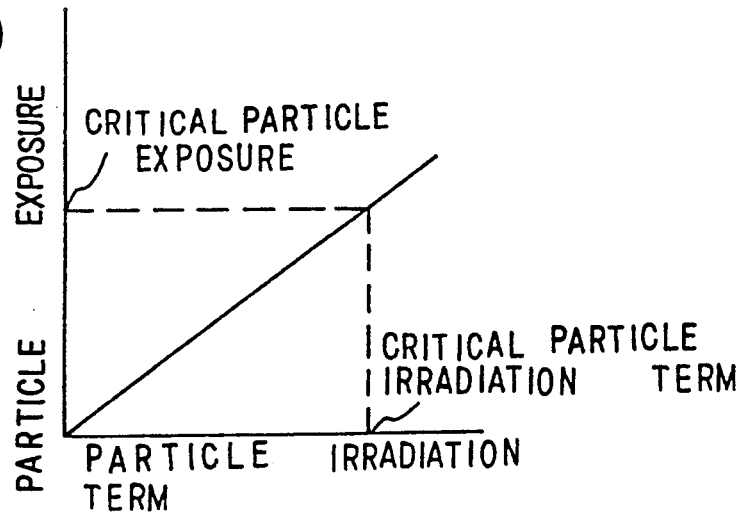

FIGS. 3(a)~3(c) are graphs showing the stored contents of the memory 3. In FIG. 3(a) showing the content of the first storage means 31, the ordinate represents the change in the mechanical characteristic value, while the abscissa represents the radiation embrittlement percentage. The "change in the mechanical characteristic value" indicated on the ordinate is intended to mean, for example, the change in hardness or increment in 0.2% yield strength before and after the irradiation with the particles such as ions or neutrons. The "radiation embrittlement percentage" indicated on the abscissa is intended to mean the embrittlement percentage due to the unstable fracture including embrittlement due to a brittle fracture and embrittlement due to a ductile fracture of the sample, and, more specifically, to mean the ratio between failure elongations before and after the particle ray irradiation (failure elongation after the particle ray irradiation/failure elongation before the particle ray irradiation).

In FIG. 3(b) showing the content of the second storage means 32, the ordinate represents the particle exposure of the model sample, while the abscissa represents the radiation embrittlement percentage. Besides, the "critical radiation embrittlement percentage" indicated in the figure signifies the radiation embrittlement percentage at which the model sample cracks, and the particle exposure corresponding to the critical radiation embrittlement percentage is called the "critical particle exposure".

In FIG. 3(c) showing the content of the third storage means 33, the ordinate represents the particle exposure of the actual sample, while the abscissa represents the particle ray irradiation term. Here, a "critical particle ray irradiation term" signifies the particle ray irradiation term corresponding to the critical particle exposure.

The above contents in FIGS. 3(a)~3(c) may well be displayed on the CRT 4 or the like output means as the occasion arises.

The arithmetic unit 2 constructed of a CPU includes first calculation means 21 for evaluating the radiation embrittlement percentage corresponding to the change in the mechanical characteristic value of the actual sample irradiated with the particles, from the stored content of the first storage means 31; second calculation means 22 for evaluating the particle exposure of the actual sample corresponding to the radiation embrittlement percentage evaluated by the first calculation means 21, from the stored content of the second storage means 32; third calculation means 23 for evaluating the particle ray irradiation term of the actual sample corresponding to the particle exposure thereof evaluated by the second calculation means 22, from the stored content of the third storage means 33; and fourth calculation means 24 for evaluating the critical irradiation term corresponding to the critical exposure stored in the second storage means 32, from the stored content of the third storage means 33, and for comparing the evaluated critical irradiation term with the aforementioned particle ray irradiation term so as to calculate the difference and/or the ratio between both the terms.

In general, when a material is irradiated with particles such as neutrons, it undergoes changes in hardness, strength and elongation. Simultaneously with such changes in the properties, the material becomes brittle due to the irradiation. In order to estimate the remaining service life of the material, therefore, the relationship between the change in the mechanical characteristic value of the hardness, the strength or the like and the percentage of radiation embrittlement is obtained for the material irradiated with the particles such as neutrons. Further, the relationship between the radiation embrittlement percentage and the particle exposure and the relationship between the particle ray irradiation term and the particle exposure are obtained. Besides, the method is so contrived as to evaluate the radiation embrittlement percentage from the change of the mechanical property such as hardness or strength, thereby estimating the remaining service life.

Figure 2:
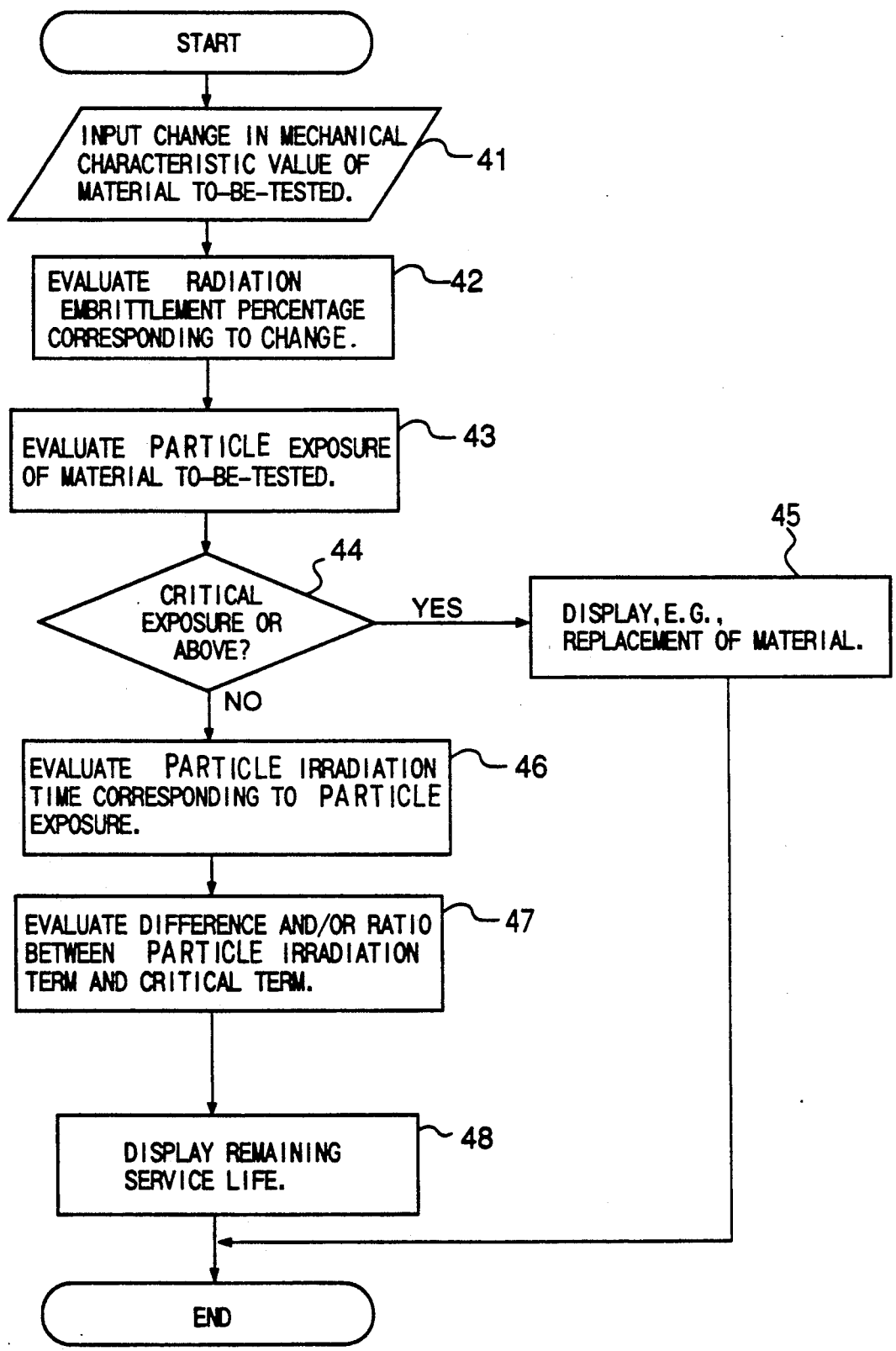
FIG. 2 is a flow chart of a remaining service life prediction method according to the embodiment of FIG. 1.

This method will be explained using the flow chart shown in FIG. 2. First, the change in the mechanical characteristic value of the actual sample irradiated with the particles is input (step 41). Subsequently, the radiation embrittlement percentage corresponding to the change in the mechanical characteristic value of the actual sample is evaluated from the relationship stored in the first storage means, between the change in the mechanical characteristic value and the radiation embrittlement percentage of the model sample which has substantially the same composition as that of the actual sample and which has been irradiated with the particles of predetermined dose (step 42). The radiation embrittlement percentage is indicative of the embrittlement percentage due to the unstable fracture. At the next step, the particle exposure of the actual sample corresponding to the radiation embrittlement percentage thereof is evaluated from the relationship between the particle exposure of the model sample and the radiation embrittlement percentage thereof, this relationship being previously stored in the second storage means, with the critical exposure corresponding to the critical radiation embrittlement percentage at which the model sample breaks (step 43). Next, on condition that the particle exposure of the actual sample is the critical exposure or above (step 44), an output is delivered to that effect, and the need for replacement of the material, for example, is displayed (step 45). On the other hand, when the particle exposure of the actual sample is below the critical exposure (step 44), the particle ray irradiation term corresponding to the particle exposure of the actual sample subjected to the particle ray irradiation is evaluated from the relationship preliminarily stored in the third storage means, between the particle exposure of the actual sample and the particle ray irradiation term thereof (step 46). Next, the difference and/or the ratio between the evaluated particle ray irradiation term and the critical particle ray irradiation term corresponding to the critical exposure are/is evaluated (step 47), and the remaining service life is output to the CRT or the like (step 48).

Since the above processing is executed by the use of the remaining service life prediction apparatus 100 according to this embodiment, an operator can know the remaining service life of a structure made of the same material as the actual sample, merely by inputting the change in the mechanical characteristic value of the actual sample to this apparatus 100 through the input means 1. The expression "change in the mechanical characteristic value" is intended to mean, for example, the difference or ratio between the values of 0.2-% yield strength, hardness, or failure elongation or tensile elongation percentage before and after the particle ray irradiation. Alternatively, change in an electrical characteristic value, such as the difference between the values of electric resistance or eddy current before and after the irradiation may well be input instead of the change in the mechanical characteristic value.

The embodiment of FIGS. 4–6(a)–6(d) and 7–13 exemplifies the prediction of the remaining service life of a material which develops stress corrosion cracking under neutron irradiation within a nuclear reactor. When neutrons collide against atoms within a metal, a large number of irradiation defects (point defects) are formed by the cascade process. The defects are moved and extinguished in a short time of about $10^{-3}$ sec. within cascades until the number thereof reaches a certain value. The point defects having survived within the cascades migrate long distances and form secondary defects such as dislocations and voids, which heighten the resistances of the motions of the dislocations, thereby incurring embrittlement and hardening.

On the other hand, interstitial atoms, interstices etc. formed in the material by irradiation interact with solute atoms, to incur the segregation phenomena of chemical components such as P, Si, Cr, Ni and Mn. Thus, the susceptibility of the material to stress corrosion cracking is affected.

In this manner, when the material, especially the metal material, is irradiated with the neutrons, it undergoes a change in susceptibility to stress corrosion cracking, along with the changes in mechanical properties such as radiation embrittlement and hardening. Accordingly, when the relationship between both sorts of change are found, a stress corrosion cracking characteristic can be determined from the change of hardness, strength, elongation or the like.

Figure 12:
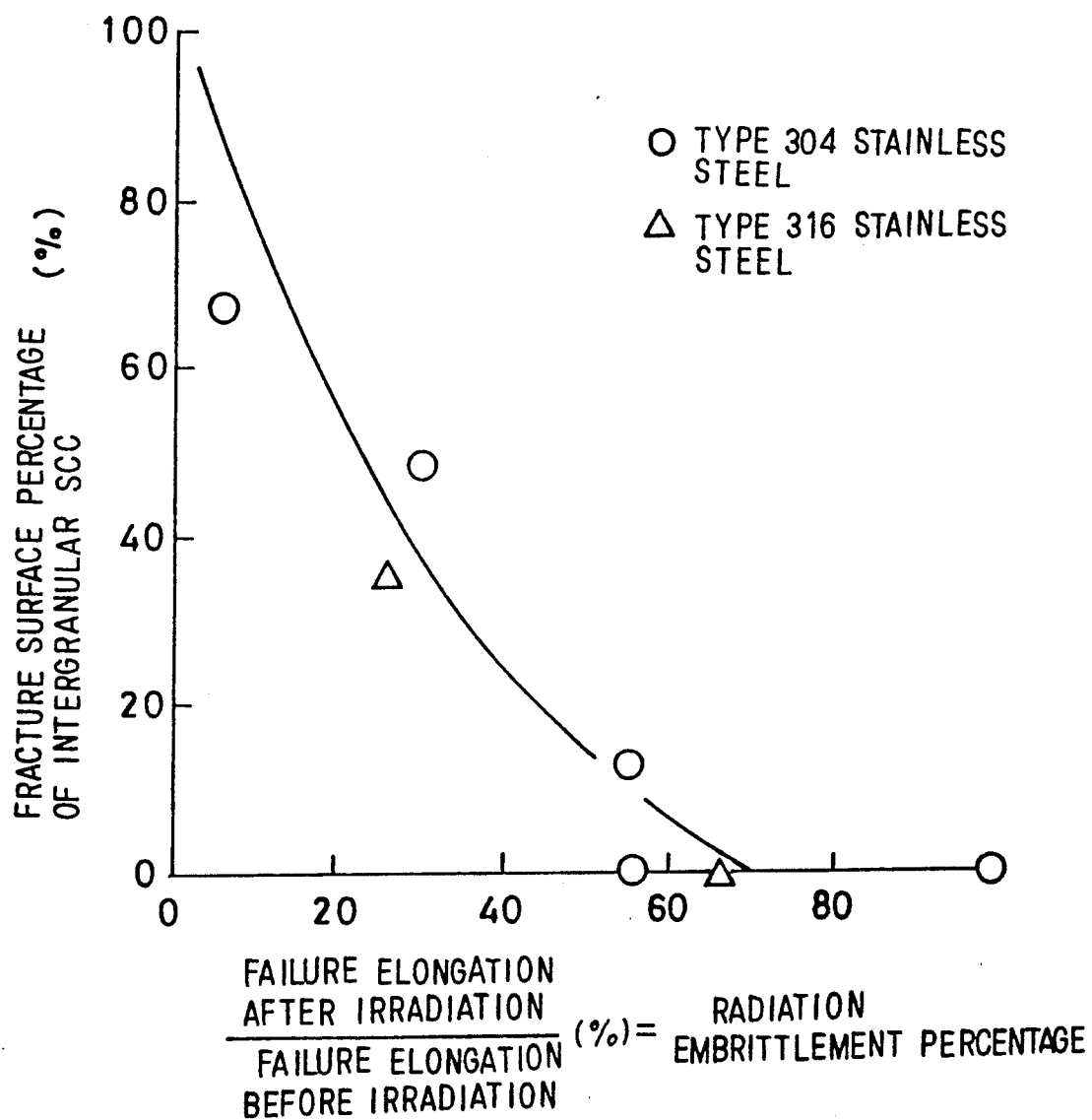
FIG. 12 is a graphical illustration of a relationship between the ratio of the failure elongations before and after irradiation and the fracture ratio of intergranular SCC of austenitic stainless steel irradiated with neutrons.

A model sample having the same composition as that of austenitic stainless steel for use in the nuclear reactor was irradiated with the neutrons, had its relationship between the stress corrosion cracking characteristic and the percentage of failure elongations (elongations at which the material ruptured) in high-temperature water (of 288° C., 85 atm. and 32 ppmDO) was examined by a Slow-Strain Rate (about $10^{-7}$ S$^{-1}$) Tensile test, resulting in the data illustrated in FIG. 12. In the present embodiment, the material to be tested is subjected to the unstable fracture including a brittle fracture and a ductile fracture to lead to a rupture. The graph of FIG. 12 illustrates for the austenitic stainless steel subjected to the neutron irradiation, the relationship between the radiation embrittlement obtained from the ratio of the failure elongations before and after the irradiation (failure elongation after the irradiation/failure elongation before the irradiation) and the fracture percentage of intergranular stress corrosion cracking. In the graph, the abscissa represents the ratio between the failure elongations before and after the irradiation, while the ordinate represents the fracture percentage of the intergranular stress corrosion cracking. The term "radiation embrittlement" is used herein to mean the embrittlement due to the unstable fracture which includes the brittle fracture and the ductile fracture. Additionally, in FIG. 12, the circular a circle indicate the results on an SUS304 type material, while triangular symbols indicate the results on an SUS316 type material.

As shown in FIG. 12, the failure elongation of the material decreases more due to the neutron irradiation, while the fracture percentage of the intergranular stress corrosion cracking further increases. It is accordingly suggested that, when the radiation embrittlement percentage of the material is great, the stress corrosion cracking resistance thereof will also degrade. In addition, it is seen from the graph of FIG. 12 that, when the ratio between the failure elongations before and after the neutron irradiation is about 60% or above, the intergranular stress corrosion cracking does not take place. This has revealed the existence of the radiation embrittlement percentage at the limit at which the intergranular stress corrosion cracking does not arise. Besides, regarding such test results, no discrepancy was observed between the test based on the neutron irradiation within the nuclear reactor and a test based on neutron irradiation by an ion accelerator to be explained in connection with FIG. 11. It is accordingly understood that the material in the nuclear reactor can be estimated by an experiment employing the cyclotron. Incidentally, the model sample was in the shape of a steel sheet which was about 3 mm wide, about 15 mm long and about 0.3 mm thick.

In this embodiment, the actual sample is mounted in the nuclear reactor at the beginning of the operation of the reactor. The mounted position of the actual sample in the nuclear reactor will be explained with reference to FIGS. 7 and 8. FIG. 8, the ordinate represents the length of this neutron monitoring tube (full length: about 4 m), and the abscissa represents the intensities of neutron exposures.

Figure 7:
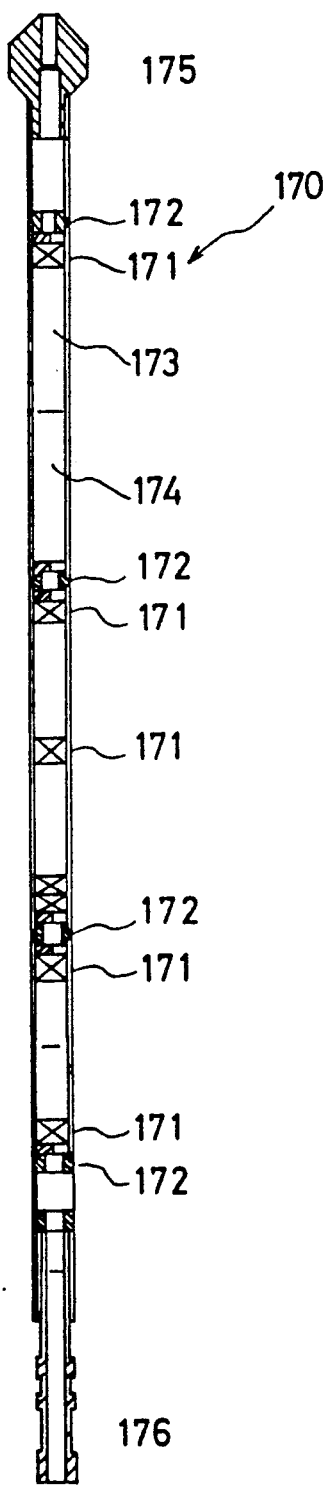
FIG. 7 is a sectional view of a neutron monitoring tube in which materials to be tested are inserted.
Figure 8:
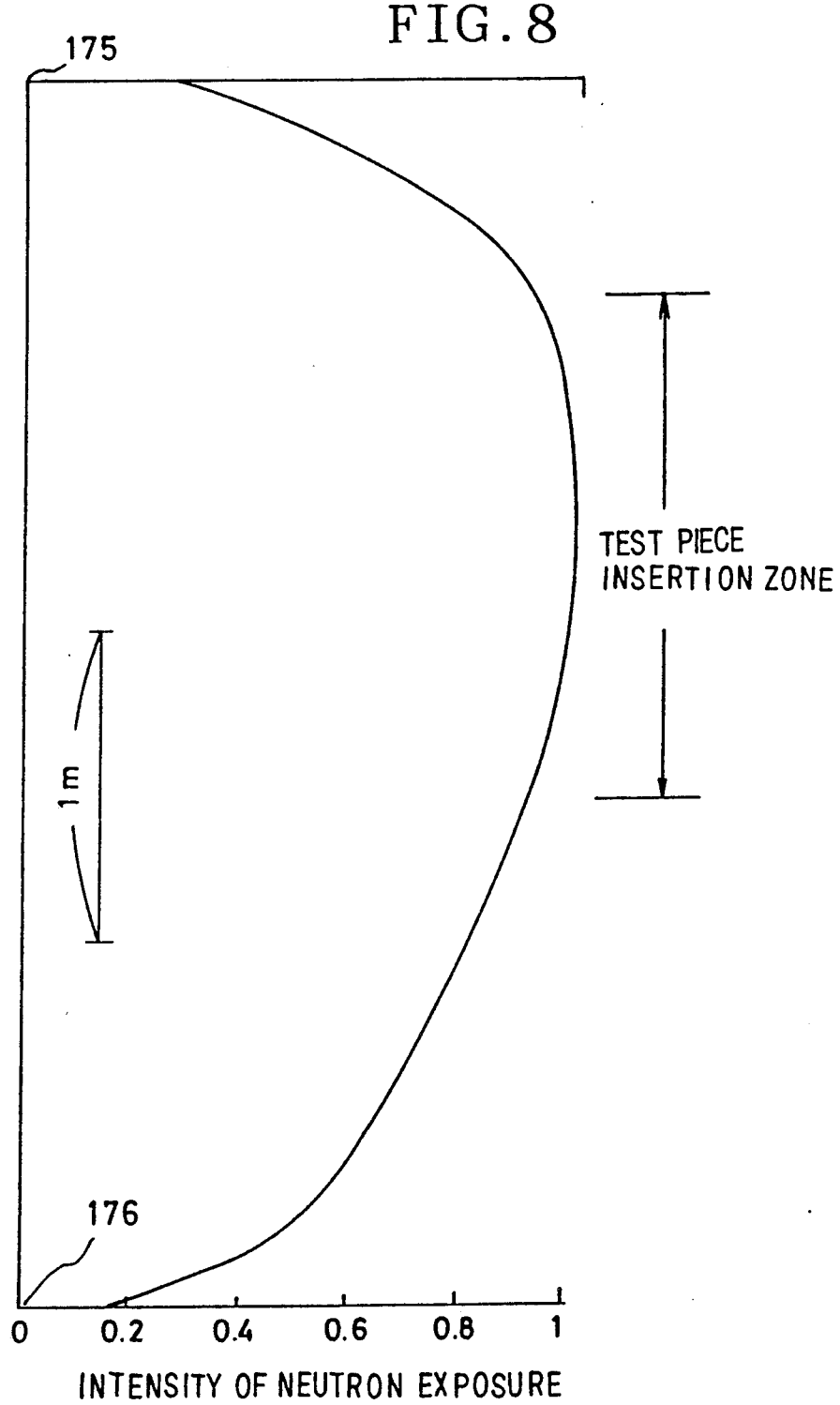
FIG. 8 is a graphical illustration of an intensity distribution of neutron irradiation in the axial direction of the neutron monitoring tube.

The actual sample is inserted in the neutron monitoring tube 170 as shown in FIG. 7. The neutron monitoring tube 170 is constructed having fluence monitors 171 for measuring neutron fluxes, spacers 172, an insertion position 173 for inserting a tensile test piece assembly, and an insertion position 174 for inserting a hardness test piece assembly. Since the wall thickness of the neutron monitoring tube 170 is about 1.5 mm and is sufficiently smaller than about 10 cm which is the metal penetrating power of neutron irradiation, the neutron irradiation within the monitoring tube and direct irradiation have almost no difference. The two test pieces at the positions 173 and 174 are inserted in a test piece insertion zone 180 having neutron exposure intensities as shown in FIG. 8.

Figure 4:
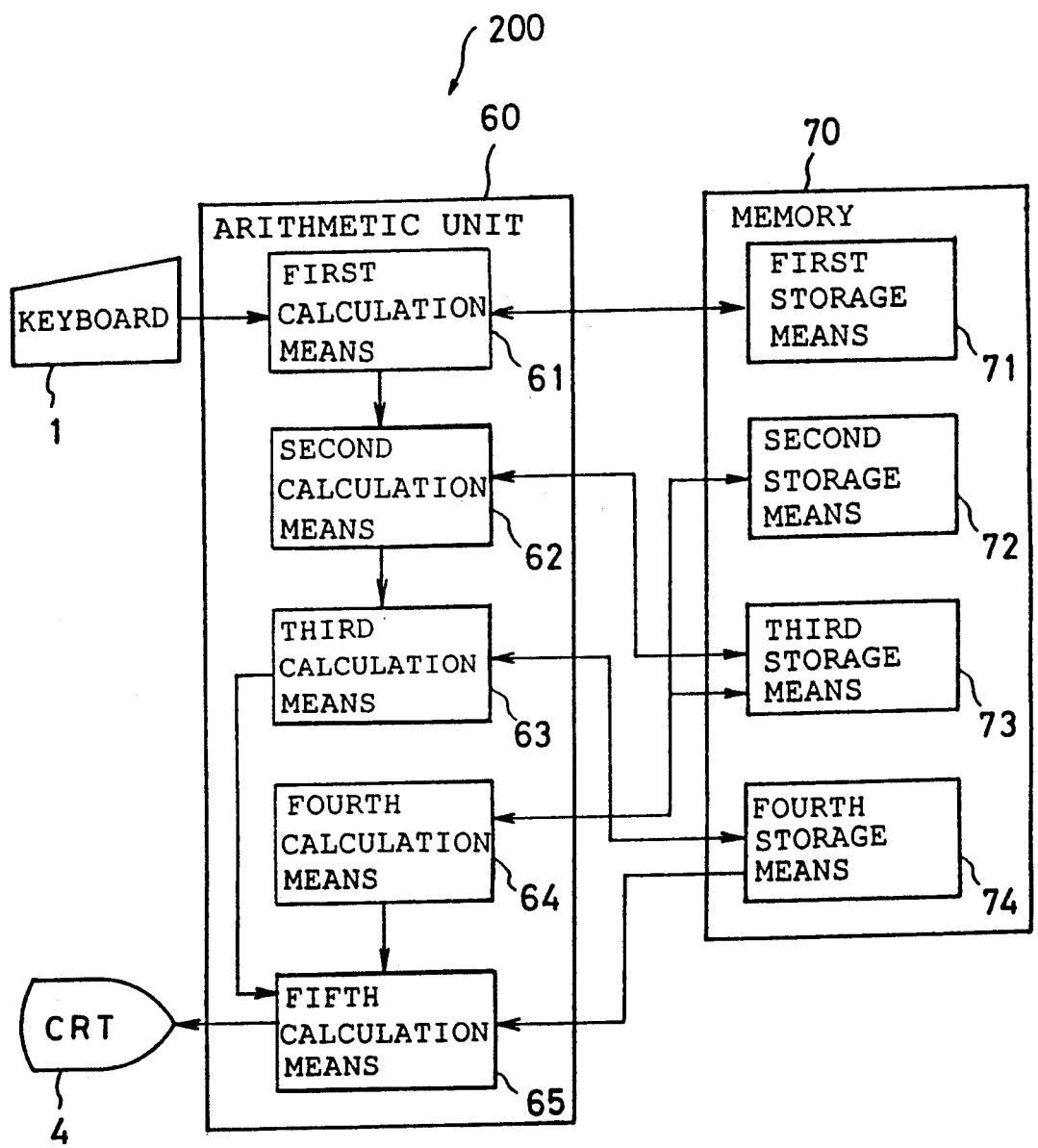
FIG. 4 is a block diagram of a remaining service life prediction apparatus according to another embodiment of the present invention.
Figure 5:
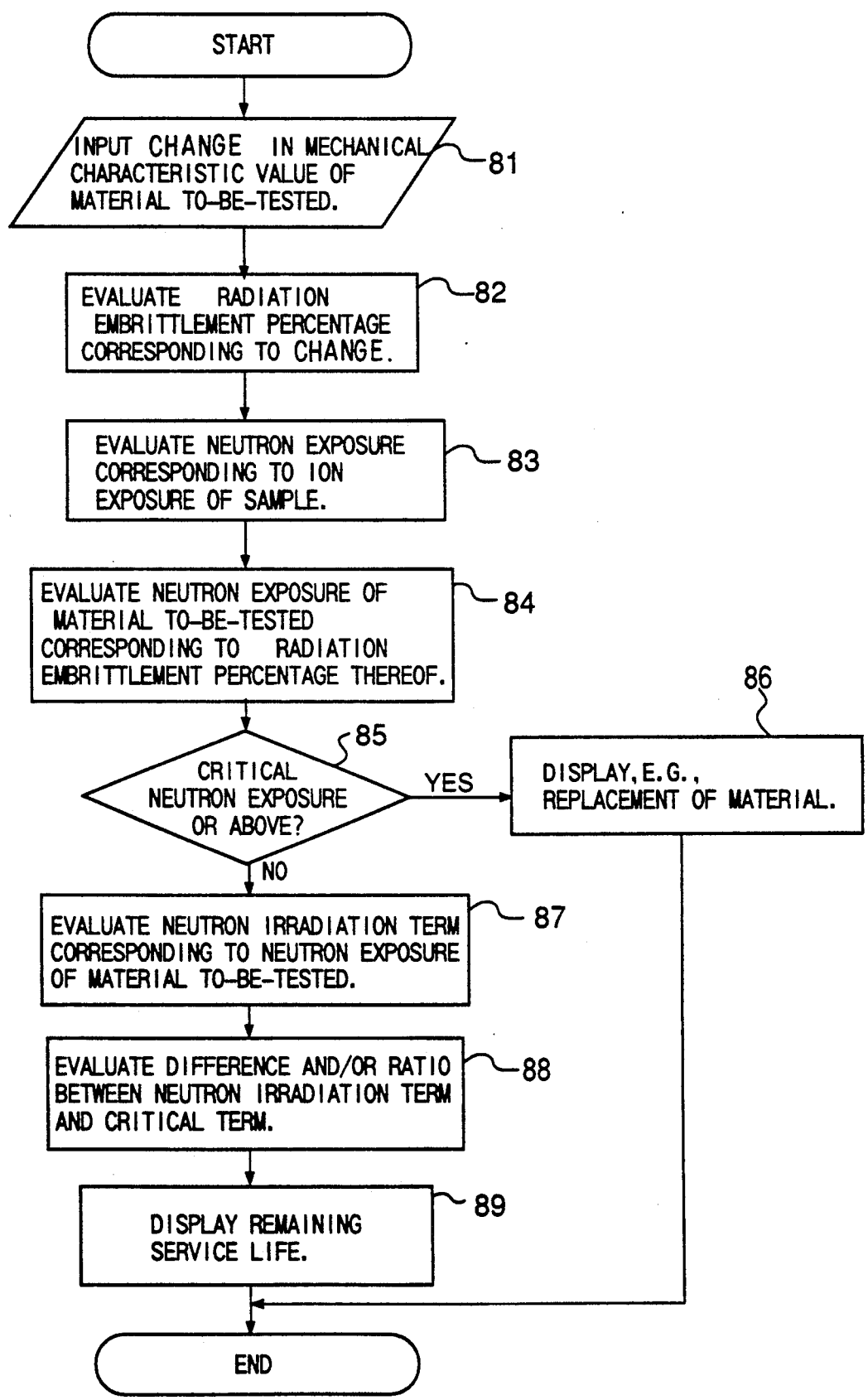
FIG. 5 is a flow chart of a remaining service life prediction method according to the embodiment of FIG. 4.

Now, a remaining service life prediction apparatus according to this embodiment will be described with reference to FIG. 4. Wherein the remaining service life prediction apparatus 200 comprises input means such as a keyboard 1 through which a change in the mechanical characteristic value of the actual sample by being irradiated with neutrons in the nuclear reactor is received, a memory 70 in which predetermined information items are stored beforehand, an arithmetic unit 60 constructed of a CPU which executes predetermined calculations in accordance with programs written in a memory (not shown), and output means such as a CRT 4 which displays the remaining service life of the material.

The memory 70 includes first storage means 71 for previously storing therein the relationship between the change in the mechanical characteristic value of a model sample irradiated with ions of predetermined dose and the percentage of radiation embrittlement indicating the degree of embrittlement of the model sample, second storage means 72 for previously storing therein the relationship between the susceptibility of the model sample to stress corrosion cracking and the radiation embrittlement percentage of the model sample, third storage means 73 for preliminarily storing therein the relationship between the radiation embrittlement percentage and the neutron exposure of the model sample into which the ion exposure thereof is converted, and fourth storage means 74 for preliminarily storing therein the relationship between the neutron exposure and the operation term of the nuclear reactor whose constituent material is the actual sample having substantially the same composition as that of the model sample.

Figure 6A:
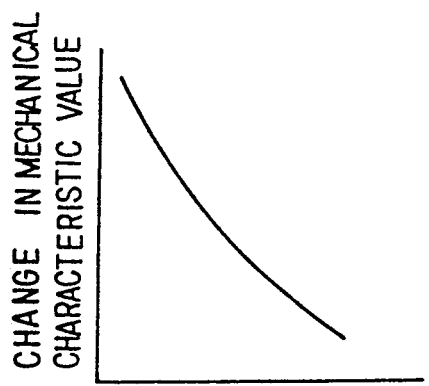
FIGS. 6(a)~6(d) are graphical illustrations of contents of data which are preliminarily stored in a memory in the remaining service life prediction apparatus of the embodiment of FIG. 4.

Next, the contents of the respective storage means will be elucidated in conjunction with FIGS. 6(a)~6(d), which are graphs illustrating the contents of data stored beforehand. In the graph of FIG. 6(a) showing the content of the first storage means 71, the ordinate represents the change in the mechanical characteristic value, while the abscissa represents the radiation embrittlement percentage. The "change in the mechanical characteristic value", indicated on the ordinate is intended to mean, for example, change in hardness before and after the ion irradiation or increment in 0.2% yield strength after the ion irradiation. The "radiation embrittlement percentage" indicated on the abscissa is intended to mean the ratio between failure elongations before and after the ion irradiation (failure elongation after the ion irradiation/failure elongation before the ion irradiation).

Figure 9:
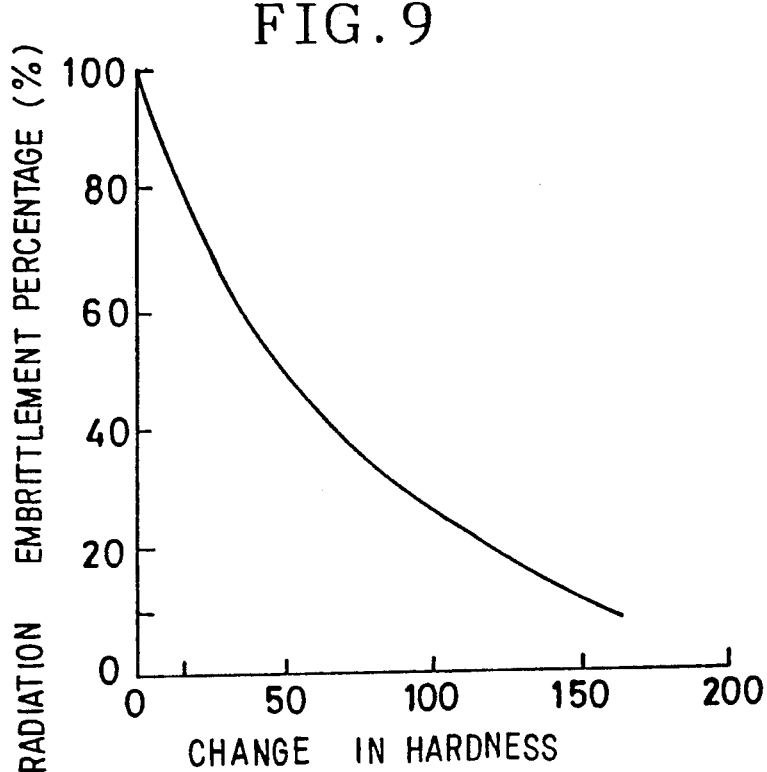
FIG. 9 is a graphical illustration of a relationship between the change in hardness and the radiation embrittlement of a sample irradiated with ions.
Figure 10:
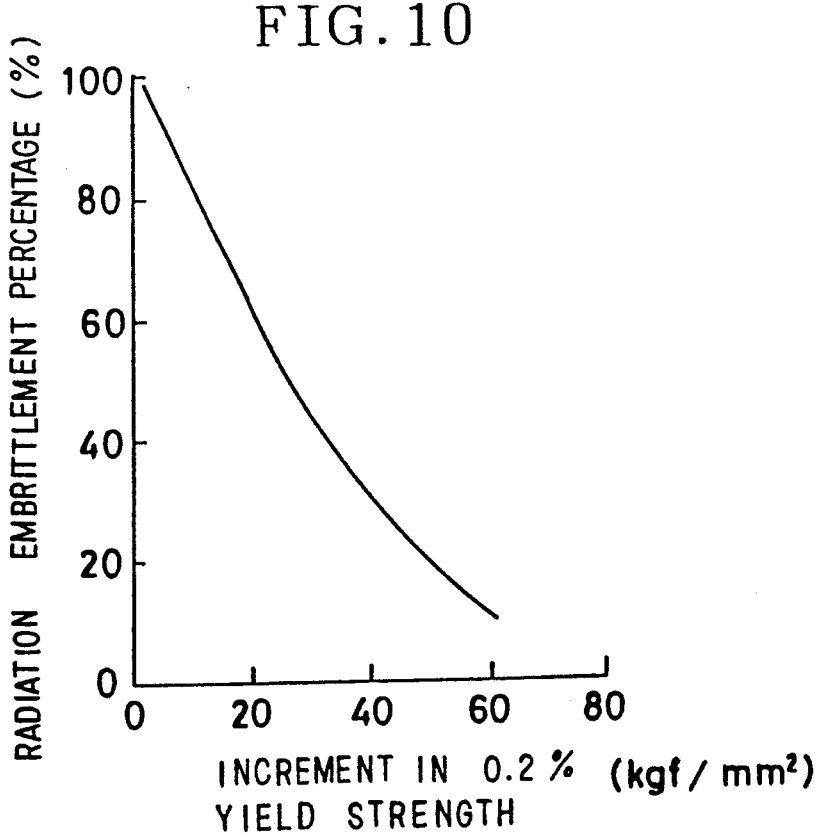
FIG. 10 is a graphical illustration of a relationship between the increment in 0.2-% yield strength and the radiation embrittlement of a sample irradiated with ions.
Figure 13:
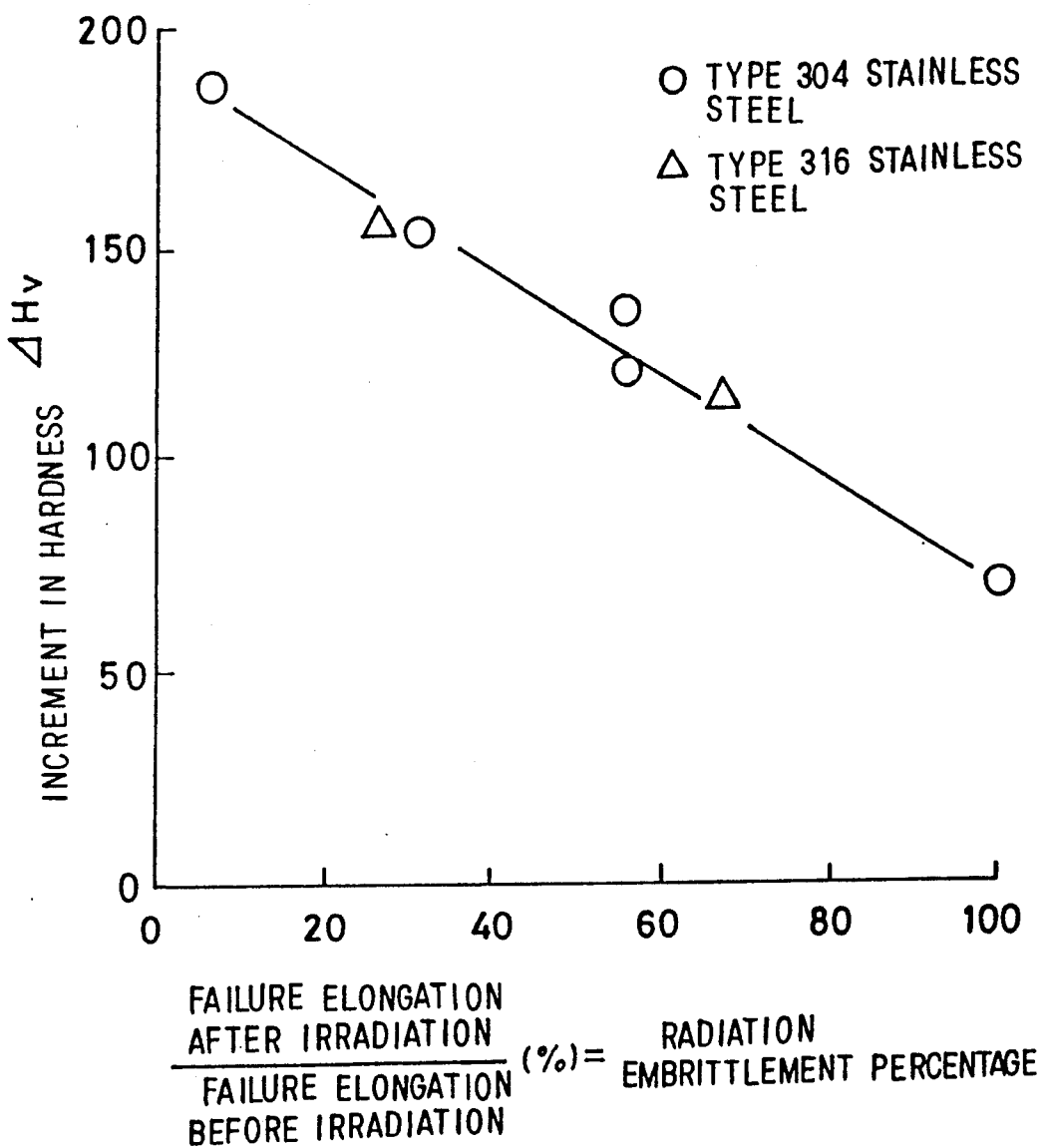
FIG. 13 is a graphical illustration of relationship between the ratio of the failure elongations before and after irradiation (the percentage of radiation embrittlement) and the increment in hardness of austenitic stainless steel irradiated with neutrons.

Actual measurement examples concerning such changes are depicted in FIGS. 9 and 10, wherein in FIG. 9 the ordinate represents the radiation embrittlement percentage, while the abscissa represents the change in the hardness. FIG. 10 the ordinate represents the radiation embrittlement percentage, while the abscissa represents the increment in the 0.2% yield strength. It is seen from FIG. 9 or FIG. 10 that, as the change in the hardness or the strength increases, the radiation embrittlement percentage lowers, so the failure elongation decreases, and the model sample becomes more brittle. In FIG. 13 the abscissa represents the ratio between the failure elongations before and after the irradiation, while the ordinate represents the increment in the hardness. Additionally, the circular marks symbols indicate the results on the SUS304 type material, while triangular marks symbols indicate the results on the SUS316 type material. These results are similar to the results depicted in FIG. 9.

Figure 6B:
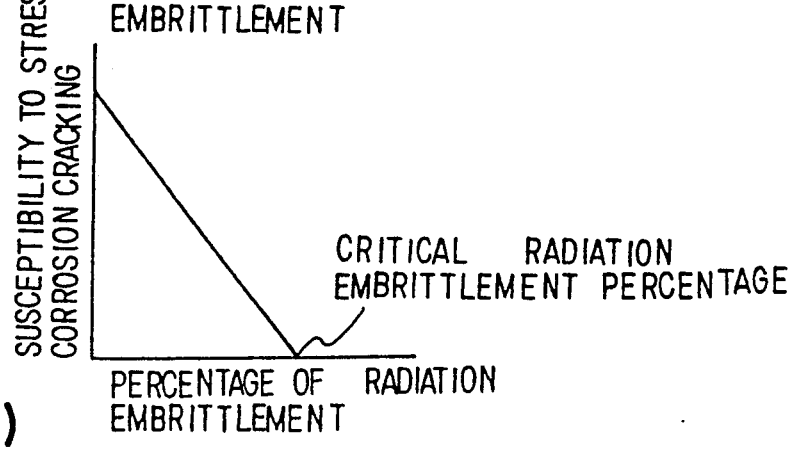

In the graph of FIG. 6(b) showing the content of the second storage means 72, the ordinate represents the susceptibility of the ion-irradiated model sample to stress corrosion cracking, while the abscissa represents the percentage of radiation embrittlement. The "susceptibility to stress corrosion cracking" indicated on the axis of ordinates signifies the ratio between the fracture percentage of the intergranular stress corrosion cracking before and after the irradiation. Besides, an expression "critical radiation embrittlement percentage" indicated in the figure signifies the radiation embrittlement percentage at which the fracture of the intergranular stress corrosion cracking begins to be observed. Usually, it corresponds to the radiation embrittlement percentage at which the likelihood of the stress corrosion cracking rises.

Figure 11:
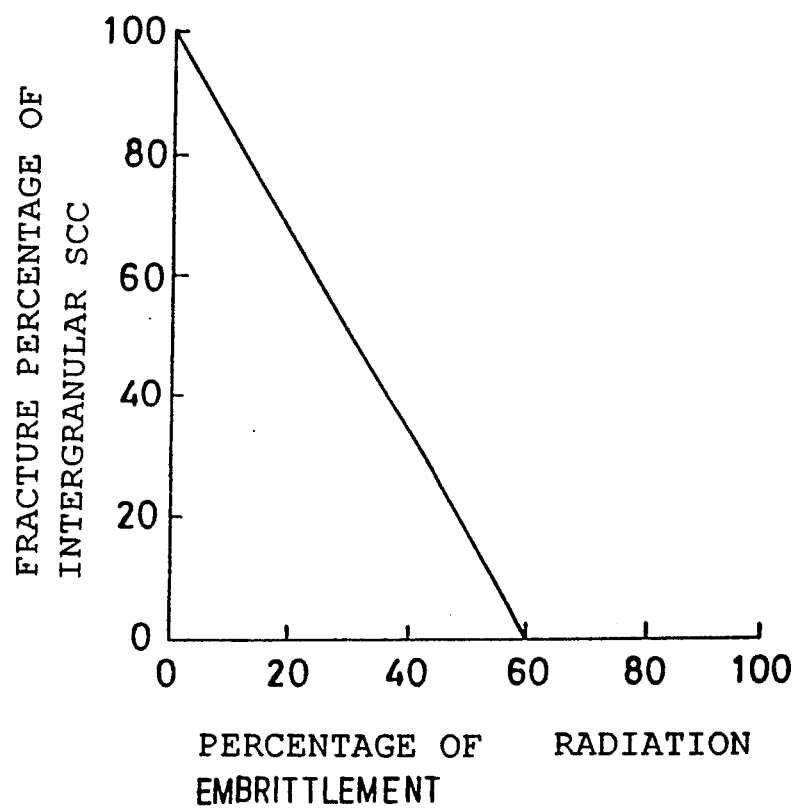
FIG. 11 is a graphical illustration of a relationship between the percentage of radiation embrittlement and the fracture ratio of intergranular stress corrosion cracking (IGSCC)

An actual measurement example concerning the cracking is graphically illustrated in FIG. 11, with the fracture percentage of the IGSCC having been obtained by observing the model sample after its failure with an electron microscope.

Figure 6C:
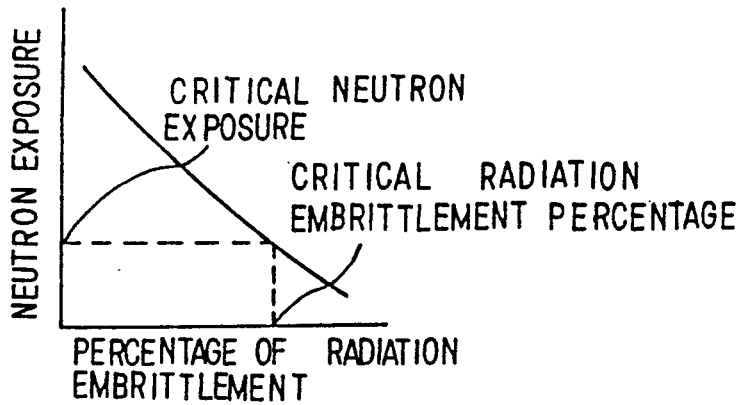

In the graph of FIG. 6(c) showing the content of the third storage means 73, the ordinate represents the neutron exposure of the model sample corresponding to the ion exposure thereof, while the abscissa represents the percentage of radiation embrittlement. The radiation embrittlement percentage is a unified variable expressing the percentage of embrittlement ascribable to the particle ray irradiation, and the ion exposure leading to a predetermined value of the embrittlement percentage can be converted into the neutron exposure. The results of such conversion are graphically depicted in FIG. 6(c). The method of the conversion is expressed by 1 dpa$\approx 1 \times 10^{21}$ n/cm$^2$. Here, the unit dpa denotes the number of target atoms emitted as daughters per atom of the incident corpuscular radiation. In addition, an expression "critical neutron exposure" signifies the neutron exposure corresponding to the critical radiation embrittlement percentage indicated in FIG. 6(b).

Figure 6D:
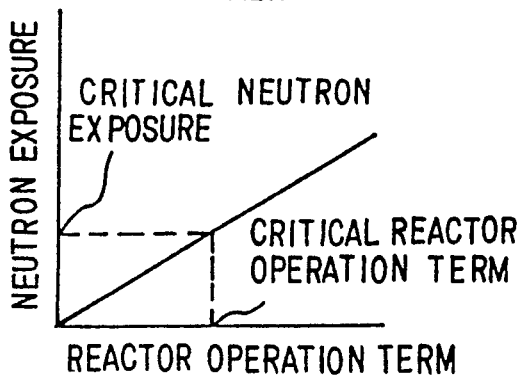

In the graph of FIG. 6(d) showing the content of the fourth storage means 74, the ordinate represents the neutron exposure of the actual sample inserted in the nuclear reactor, while the abscissa represents the operation term of the nuclear reactor. Here, an expression "critical reactor operation term" signifies the reactor operation term corresponding to the critical neutron exposure.

The above contents in FIGS. 6(a)~6(d) may well be displayed on the output means such as CRT 4 as the occasion arises.

The arithmetic unit 60 includes first calculation means 61 for evaluating the radiation embrittlement percentage corresponding to the change in the mechanical characteristic value of the actual sample, from the stored content of the first storage means 71; second calculation means 62 for evaluating the neutron exposure of the actual sample corresponding to the radiation embrittlement percentage evaluated by the first calculation means 61, from the stored content of the third storage means 73; third calculation means 63 for evaluating the reactor operation term corresponding to the neutron exposure evaluated by the second calculation means 62, from the stored content of the fourth storage means 74; fourth calculation means 64 for evaluating the critical neutron exposure of the actual sample corresponding to the critical radiation embrittlement percentage at which the stress corrosion cracking occurs and which is stored in the second storage means 72, from the stored content of the third storage means 73; and fifth calculation means 65 for evaluating the critical reactor operation term corresponding to the critical neutron exposure evaluated by the fourth calculation means 64, from the stored content of the fourth storage means 74, and for comparing the critical reactor operation term with the reactor operation term so as to calculate the remaining service life in accordance with the difference between both the terms.

Now, a method of estimating the remaining service life of the material by the use of the remaining service life prediction apparatus 200 will be described. Reference will be made to a flow chart shown in FIG. 5 which illustrates the remaining service life prediction method according to this embodiment. First, the change in the mechanical characteristic value of the actual sample irradiated with neutrons within the nuclear reactor is input (step 81). Subsequently, the radiation embrittlement percentage corresponding to the change in the mechanical characteristic value of the actual sample is evaluated from the relationship, previously stored in the first storage means 71, between the change in the mechanical characteristic value of the model sample having substantially the same composition as that of the actual sample and being irradiated with ions of predetermined dose and the radiation embrittlement percentage of the model sample (step 82). At the next step, the neutron exposure of the model sample corresponding to the ion exposure thereof is evaluated from the relationship previously stored in the third storage means 73, between the neutron exposure converted from the ion exposure and the radiation embrittlement percentage (step 83). Next, the neutron exposure of the actual sample corresponding to the radiation embrittlement percentage thereof is evaluated from the stored content of the second storage means 72 previously storing therein the relationship between the ion exposure and the radiation embrittlement percentage of the sample, together with the critical ion exposure corresponding to the critical radiation embrittlement percentage at which the fracture of the intergranular stress corrosion cracking begins to be observed in the model sample (step 84). Next, on condition that the neutron exposure of the actual sample is the critical neutron exposure or above (step 85), an output is delivered to that effect (step 86). On the other hand, when the neutron exposure of the actual sample is below the critical neutron exposure (step 85), the neutron irradiation term of the actual sample corresponding to the neutron exposure thereof is evaluated from the relationship previously stored in the fourth storage means 74, between the neutron exposure of the actual sample and the neutron irradiation term thereof (step 87). Further, the difference or/and the ratio between the neutron irradiation term and the critical neutron irradiation term corresponding to the critical neutron exposure is/are evaluated (step 88), and the remaining service life is displayed (step 89).

Since the above processing is executed by the use of the remaining service life prediction apparatus 200 according to this embodiment, an operator can predict the service life of a reactor material subjected to neutron irradiation at high temperatures, concerning the stress corrosion cracking, merely by measuring the change in hardness, strength or a similar mechanical characteristic value of the actual sample which is the metal test piece irradiated with neutrons within the nuclear reactor. This is very effective for the preventive safety of a nuclear power plant. The expression "change in the mechanical characteristic value" is intended to mean, for example, the difference or ratio between the values of 0.2% yield strength, hardness, or failure elongation or tensile elongation percentage before and after the particle ray irradiation. Alternatively, change in an electrical characteristic value, such as the difference between the values of electric resistance or eddy current before and after the irradiation may well be input instead of the change in the mechanical characteristic value.

Now, there will be explained a case of applying the technique of the second embodiment to the remaining service life prediction of a nuclear reactor under operation. The embrittlement percentage of a reactor member having hitherto been used is evaluated. For this purpose, the used member of the reactor under operation is employed as a test material piece by way of example. Embrittlement percentage equivalent to the evaluated embrittlement percentage is given to the actual sample by the combination of cold working and annealing. The actual sample thus prepared is inserted into the reactor under operation, and is used for the prediction of the remaining service life. The mechanical characteristic in the form of a physical quantity such as a hardness of the actual sample placed in the reactor under operation is measured, for example, by using ultrasonic wave. More specifically, ultrasonic wave is transmitted to the actual sample placed in the reactor under operation and reflection wave is received from the sample to determine the hardness of the sample based on characteristics of the reflection wave. In this measurement, the hardness can be measured without removing the sample from the reactor and destructing the sample.

Each of the second and third embodiments has been described as to the construction in which the user inputs the measured result through the keyboard 1. However, this construction is not restrictive, but the measured result can of course be directly input from the model sample of the measuring device 14 in the same way as in the first embodiment.

The present invention is applicable, not only to the austenitic stainless steel, but also to inconel alloys being the materials of springs and bolts, zirconium alloys being the materials of fuel cladding tubes, and so on.

The present invention brings forth the effect that the remaining service life of a material which becomes brittle under irradiation with particles can be judged from a physical quantity obtained in the form of, for example, compliance, hardness or strength which is easily measured.

We claim:

1. A method for estimating a remaining service life of an object which is placed in an environment subjected to exposure to high-energy radiant ray and made of a material which will deteriorate in mechanical properties under the exposure to high-energy radiant ray, comprising:

a first step in which a material having substantially the same composition as said object is subjected to exposure to the high-energy radiant ray under a plurality of exposure conditions to prepare a plurality of model samples, and physical quantities of the respective model samples, indicative of the mechanical properties of the respective samples, are obtained in relation with exposure times to the respective model samples to obtain a relationship between an exposure time and a physical quantity for said object;

a second step for obtaining a critical exposure period of time which will cause unstable fracture in the material of said object from the relationship obtained in the first step;

a third step for placing an actual sample of a material having substantially the same composition as said model samples in said environment where said object is placed and subjected to exposure to the high-energy radiant ray;

a fourth step for measuring a physical quantity of the actual sample after the exposure to the high-energy radiant ray;

a fifth step for obtaining an actual exposure time corresponding to the physical quantity of the actual sample obtained in the fourth step on the basis of the relationship between the physical quantity and the exposure time obtained in the first step to regard said actual exposure time thus obtained as an actual exposure time of said object; and a sixth step for obtaining a difference between the critical exposure time obtained in the second step and the actual exposure time of said object obtained in the fourth step.

2. A method for estimating a remaining service life of an object according to claim 1, in which said first step includes a first-first step for obtaining a relationship between the physical quantities of the model samples and exposure doses applied thereto, and a first-second step for obtaining a relationship between exposure doses and exposure times corresponding to the respective exposure doses for said object; and said second step includes a second-first step for obtaining a critical value of the physical quantity which will cause unstable fracture in the material from the relationship obtained in the first-first step and a critical exposure dose corresponding to said critical value of the physical quantity, and a second-second step for obtaining a critical exposure time for said object corresponding to said critical exposure dose from the relationship between the exposure doses and the exposure times obtained in the first-second step.

3. A method for estimating a remaining service life of an object according to claim 2, in which said critical value of the physical quantity is obtained in the form of a critical embrittlement value.

4. A method for estimating a remaining service life of an object according to claim 1, in which said material is a ferrous material.

5. A method for estimating a remaining service life of an object according to claim 1, in which said object is an inner structure of a reactor.

6. A method for estimating a remaining service life of an object according to claim 1, in which said physical quantity comprises a radiation embrittlement percentage of a ferrous material as an essential parameter.

7. A method for estimating a remaining service life of an object which is placed in an environment subjected to exposure to high-energy radiant ray and made of a material which will deteriorate in mechanical properties under the exposure to high-energy radiant ray, comprising:

a first step in which a material having substantially the same composition as said object is subjected to exposure to the high-energy radiant ray under a plurality of exposure conditions to prepare a plurality of model samples, and physical quantities of the respective model samples, indicative of the mechanical properties of the respective samples, are obtained in relation with exposure times to the respective model samples to obtain a relationship between an exposure time and a physical quantity for said object;

a second step for obtaining a critical exposure period of time which will cause unstable fracture in the material of said object from the relationship obtained in the first step;

a third step for placing an actual sample of a material having substantially the same composition as said model samples in said environment where said object is placed and subjected to exposure to the high-energy radiant ray;

a fourth step for taking in a physical quantity of the actual sample after the exposure to the high-energy radiant ray;

a fifth step for obtaining an actual exposure time corresponding to the physical quantity of the actual sample obtained in the fourth step on the basis of the relationship between the physical quantity and the exposure time obtained in the first step to regard said actual exposure time thus obtained as an actual exposure time of said object; and a sixth step for obtaining a difference between the critical exposure time obtained in the second step and the actual exposure time of said object obtained in the fourth step.

8. A method for estimating a remaining service life of an object according to claim 7, in which said fist step includes a first-first step for obtaining a relationship between the physical quantities of the model samples and exposure doses applied thereto, and a first-second step for obtaining a relationship between exposure doses and exposure times corresponding to the respective exposure doses for said object; and said second step includes a second-first step for obtaining a critical value of the physical quantity which will cause unstable fracture in the material from the relationship obtained in the first-first step and a critical exposure dose corresponding to said critical value of the physical quantity, and a second-second step for obtaining a critical exposure time for said object corresponding to said critical exposure dose from the relationship between the exposure doses and the exposure times obtained in the first-second step.

9. A method for estimating a remaining service life of an object according to claim 8, in which said critical value of the physical quantity is obtained in the form of a critical embrittlement value.

10. A method for estimating a remaining service life of an object according to claim 7, in which said material is a ferrous material.

11. A method for estimating a remaining service life of an object according to claim 7, in which said object is an inner structure of a reactor.

12. A method for estimating a remaining service life of an object according to claim 7, in which said physical quantity comprises a radiation embrittlement percentage of a ferrous material as an essential parameter.

13. A method for estimating a remaining service life of an object which is placed in an environment subjected to exposure to high-energy radiant ray and made of a material which will deteriorate in mechanical properties under the exposure to high-energy radiant ray, comprising:

a first step in which a material having substantially the same composition as said object is subjected to exposure to the high-energy radiant ray under a plurality of exposure conditions to prepare a plurality of model samples, and physical quantities of the respective model samples, indicative of the mechanical properties of the respective samples, are obtained in relation with exposure times to the respective model samples to obtain a relationship between an exposure time and a physical quantity for said object;

a second step for obtaining a critical exposure period of time which will cause unstable fracture in the material of said object from the relationship obtained in the first step;

a third step for placing an actual sample of a material having substantially the same composition as said model samples and means for measuring a physical quantity of said actual sample in said environment where said object is placed and subjected to exposure to the high-energy radiant ray;

a fourth step for measuring the physical quantity of the actual sample after the exposure to the high-energy radiant ray;

a fifth step for obtaining an actual exposure time corresponding to the physical quantity of the actual sample obtained in the fourth step on the basis of the relationship between the physical quantity and the exposure time obtained in the first step to regard said actual exposure time thus obtained as an actual exposure time of said object; and a sixth step for obtaining a difference between the critical exposure time obtained in the second step and the actual exposure time of said object obtained in the fourth step.

14. A method for estimating a remaining service life of an object according to claim 13, in which
said first step includes a first-first step for obtaining a relationship between the physical quantities of the model samples and exposure doses applied thereto, and a first-second step for obtaining a relationship between exposure doses and exposure times corresponding to the respective exposure doses for said object; and
said second step includes a second-first step for obtaining a critical value of the physical quantity which will cause unstable fracture in the material from the relationship obtained in the first-first step and a critical exposure dose corresponding to said critical value of the physical quantity, and a second-second step for obtaining a critical exposure time for said object corresponding to said critical exposure dose from the relationship between the exposure doses and the exposure times obtained in the first-second step.

15. A method for estimating a remaining service life of an object according to claim 14, in which said critical value of the physical quantity is obtained in the form of a critical embrittlement value.

16. A method for estimating a remaining service life of an object according to claim 13, in which said material is a ferrous material.

17. A method for estimating a remaining service life of an object according to claim 13, in which said object is an inner structure of a reactor.

18. A method for estimating a remaining service life of an object according to claim 13, in which said physical quantity comprises a radiation embrittlement percentage of a ferrous material as an essential parameter.

19. An apparatus for estimating a remaining service life of an object which is placed in an environment subjected to exposure to high-energy radiant ray and made of a material which will deteriorate in mechanical properties under the exposure to high-energy radiant ray, comprising:

a first storage means for storing a relationship between an exposure time and a physical quantity for said object which has been obtained by preparing a plurality of model samples made of a material having substantially the same composition as said object and subjected to exposure to the high-energy radiant ray under a plurality of exposure conditions and by obtaining physical quantities of the respective model samples, indicative of the mechanical properties of the respective samples, in relation with exposure times to the respective model samples;

a first computing means for obtaining a critical exposure period of time which will cause unstable fracture in the material of said object from the relationship stored in the first storage means;

a taking-in means for taking in a physical quantity of an actual sample made of a material having substantially the same composition as said model samples and placed in said environment where said object is placed and subjected to exposure to the high-energy radiant ray, which is obtained after the exposure to the high-energy radiant ray; and means for obtaining an actual exposure time corresponding to the physical quantity of the actual sample taken in by said taking-in means on the basis of the relationship between the physical quantity and the exposure time stored in the first storage means to regard said actual exposure time thus obtained as an actual exposure time of said object and for obtaining a difference between the critical exposure time obtained by the first computing means and the actual exposure time of said object.

20. An apparatus for estimating a remaining service life of an object according to claim 19, in which
said first storage means includes a first-first storage means for storing a relationship between the physical quantities of the model samples and exposure doses applied thereto, and a first-second storage means for storing a relationship between exposure doses and exposure times corresponding to the respective exposure doses for said object; and
said second storage means includes a second-first storage for storing a critical value of the physical quantity which will cause unstable fracture in the material from the relationship stored in the first-first storage means and a critical exposure dose corresponding to said critical value of the physical quantity, and a second-second storage means for storing a critical exposure time for said object corresponding to said critical exposure dose from the relationship between the exposure doses and the exposure times stored in the first-second storage means.

21. An apparatus for estimating a remaining service life of an object according to claim 20, in which said critical value of the physical quantity is obtained in the form of a critical embrittlement value.

22. An apparatus for estimating a remaining service life of an object according to claim 19, in which said material is a ferrous material.

23. An apparatus for estimating a remaining service life of an object according to claim 19, in which said object is an inner structure of a reactor.

24. An apparatus for estimating a remaining service life of an object according to claim 19 in which said physical quantity comprises a radiation embrittlement percentage of a ferrous material as an essential parameter.

25. An apparatus for estimating a remaining service life of an object which is placed in an environment subjected to exposure to high-energy radiant ray and made of a material which will deteriorate in mechanical properties under the exposure to high-energy radiant ray, comprising:
- a first storage means for storing a relationship between an exposure time and a physical quantity for said object which has been obtained by preparing a plurality of model samples made of a material having substantially the same composition as said object and subjected to exposure to the high-energy radiant ray under a plurality of exposure conditions and by obtaining physical quantities of the respective model samples, indicative of the mechanical properties of the respective samples, in relation with exposure times to the respective model samples;
- a first computing means for obtaining a critical exposure period of time which will cause unstable fracture in the material of said object from the relationship stored in the first storage means;
- an actual sample which is made of a material having substantially the same composition as said model samples and placed in said environment where said object is placed and subjected to exposure to the high-energy radiant ray;
- an outputting means for outputting a physical quantity of said actual sample which is indicative of a mechanical property of the same;
- a taking-in means for taking in a physical quantity of an actual sample after the exposure to the high-energy radiant ray which is output from said outputting means; and
- means for obtaining an actual exposure time corresponding to the physical quantity of the actual sample taken in by said taking-in means on the basis of the relationship between the physical quantity and the exposure time stored in the first storage means to regard said actual exposure time thus obtained as an actual exposure time of said object and for obtaining a difference between the critical exposure time obtained by the first computing means and the actual exposure time of said object.

26. An apparatus for estimating a remaining service life of an object according to claim 25, in which
- said first storage means includes a first-first storage means for storing a relationship between the physical quantities of the model samples and exposure doses applied thereto, and a first-second storage means for storing a relationship between exposure doses and exposure times corresponding to the respective exposure doses for said object; and
- said second storage means includes a second-first storage for storing a critical value of the physical quantity which will cause unstable fracture in the material from the relationship stored in the first-first storage means and a critical exposure dose corresponding to said critical value of the physical quantity, and a second-second storage means for storing a critical exposure time for said object corresponding to said critical exposure dose from the relationship between the exposure doses and the exposure times stored in the first-second storage means.

27. An apparatus for estimating a remaining service life of an object according to claim 26, in which said physical quantity output from said outputting means is a load applied to the actual sample.

28. An apparatus for estimating a remaining service life of an object which is placed in an environment subjected to exposure to high-energy radiant ray and made of a material which will deteriorate in mechanical properties under the exposure to high-energy radiant ray, comprising:
- a first storage means for storing a relationship between an exposure time and a physical quantity for said object which has been obtained by preparing a plurality of model samples made of a material having substantially the same composition as said object and subjected to exposure to the high-energy radiant ray under a plurality of exposure conditions and by obtaining physical quantities of the respective model samples, indicative of the mechanical properties of the respective samples, in relation with exposure times to the respective model samples;
- a first computing means for obtaining a critical exposure period of time which will cause unstable fracture in the material of said object from the relationship stored in the first storage means;
- an outputting means for outputting a physical quantity of an actual sample made of a material having substantially the same composition as said model samples and placed in said environment where said object is placed and subjected to exposure to the high-energy radiant ray which is obtained after exposure to the high-energy radiant ray; and
- means for obtaining an actual exposure time corresponding to the physical quantity of the actual sample output from said outputting means on the basis of the relationship between the physical quantity and the exposure time stored in the first storage means to regard said actual exposure time thus obtained as an actual exposure time of said object and for obtaining a difference between the critical exposure time obtained by the first computing means and the actual exposure time of said object.

29. An apparatus for estimating a remaining service life of an object according to claim 28, in which
- said first storage means includes a first-first storage means for storing a relationship between the physical quantities of the model samples and exposure doses applied thereto, and a first-second storage means for storing a relationship between exposure doses and exposure times corresponding to the respective exposure doses for said object; and
- said second storage means includes a second-first storage for storing a critical value of the physical quantity which will cause unstable fracture in the material from the relationship stored in the first-first storage means and a critical exposure dose corresponding to said critical value of the physical quantity, and a second-second storage means for storing a critical exposure time for said object corresponding to said critical exposure dose from the relationship between the exposure doses and the exposure times stored in the first-second storage means.

30. An apparatus for estimating a remaining service life of an object according to claim 28, in which said actual sample has a notch preliminarily formed before being placed in the environment subject to the exposure to the high-energy radiant ray.

31. A method for estimating a remaining service life of an object which is placed in an environment subject to exposure to high-energy radiant ray and made of a material having a stress corrosion cracking under exposure to the high-energy radiant ray, the method comprising the steps of:

a first step in which a material having substantially the same composition as the object is subjected to exposure to the high-energy radiant ray under a plurality of exposure conditions to prepare a plurality of model samples, and mechanical characteristics of the respective model samples obtained in relation with exposure time to the respective model samples to obtain a relationship between an exposure time and a mechanical characteristic for said object;

a second step for obtaining a critical exposure period of time which will cause a failure in the material of said object due to stress corrosion cracking from the relationship obtained in the first step;

a third step of placing an actual sample of a material having substantially the same composition as said model samples in said environment where said object is placed and subjected to exposure to the high energy radiant ray;

a fourth step for measuring a mechanical characteristic of the actual sample after the exposure to the high energy radiant ray;

a fifth step for obtaining an actual exposure time corresponding to the mechanical characteristic of the actual sample obtained in the fourth step in dependence upon the relationship between the mechanical characteristic and the exposure time obtained in the first step with regard to said actual exposure time thus obtained as an actual exposure time of said object; and a sixth step for obtaining a difference between the critical exposure time obtained in the second step and the actual exposure time of said object obtained in the fourth step.

32. A method for estimating a remaining service life of an object according to claim 31, wherein said first step includes a first-first step for obtaining a relationship between the mechanical characteristics of the model samples and exposure doses applied thereto, and a first-second step for obtaining a relationship between exposure doses and exposure times corresponding to the respective exposure doses for said object.

33. A method for estimating a remaining service life of an object according to claim 31, in which said mechanical characteristic is the hardness, said critical exposure time in said second step is the time when a crack occurs in said material due to a stress corrosion crack.

34. A method for estimating a remaining service life of an object according to claim 31, wherein said mechanical characteristic is a stress yield, said exposure time in said second step is a time when a crack occurs in said material due to stress corrosion cracking.

35. A method for estimating a remaining service life of an object according to claim 31, in which said model samples have a crack previously made, said mechanical characteristic being the compliance, said critical exposure time being the time in which said crack previously made develops further due to stress corrosion cracking and reaches a critical crack length previously obtained by experiments corresponding to a fracture toughness value at which a failure occurs in said material.

* * * * *